United States Patent [19]

Bird et al.

[11] Patent Number: 5,208,259
[45] Date of Patent: May 4, 1993

[54] DIARYL ETHER HETROCYCLES

[75] Inventors: Thomas G. C. Bird, Witry-Les-Reims, France; Philip N. Edwards, Bramhall, England

[73] Assignees: Imperial Chemical Industries, London, England; ICI Pharma, Cergy Cedex, France

[21] Appl. No.: 547,229

[22] Filed: Jul. 3, 1990

[30] Foreign Application Priority Data

Jul. 18, 1989 [EP] European Pat. Off. ......... 894020460
Apr. 11, 1990 [EP] European Pat. Off. ......... 904010006

[51] Int. Cl.$^5$ .................... A61K 31/35; C07D 309/10
[52] U.S. Cl. .................... 514/460; 549/420; 549/419; 549/417; 549/416; 549/214; 549/53; 549/46; 548/517; 514/459; 514/443; 514/422
[58] Field of Search .................... 549/416, 51, 48, 44, 549/214, 53, 46, 417, 419, 420; 548/525, 517; 514/459, 460, 443, 422

[56] References Cited

U.S. PATENT DOCUMENTS

| | | |
|---|---|---|
| 3,661,917 | 5/1972 | Kaiser et al. |
| 3,743,737 | 7/1973 | Kaiser et al. |
| 4,918,081 | 4/1990 | Huang. |
| 4,920,130 | 4/1990 | Huang et al. ............ 514/311 |
| 4,920,131 | 4/1990 | Huang et al. ............ 514/311 |
| 4,920,132 | 4/1990 | Huang et al. ............ 514/314 |
| 4,920,133 | 4/1990 | Huang et al. ............ 514/314 |

FOREIGN PATENT DOCUMENTS

| | | |
|---|---|---|
| 0110405 | 6/1984 | European Pat. Off. |
| 0181568 | 5/1986 | European Pat. Off. |
| 0190722 | 8/1986 | European Pat. Off. |
| 0200101 | 12/1986 | European Pat. Off. |
| 0271287 | 6/1988 | European Pat. Off. |
| 0349062 | 1/1990 | European Pat. Off. |

Primary Examiner—Nicky Chan
Attorney, Agent, or Firm—Cushman, Darby & Cushman

[57] ABSTRACT

The invention concerns a diaryl ether heterocycle of the formula I, or a pharmaceutically-acceptable salt thereof,

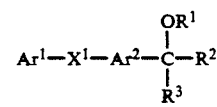

wherein
$Ar^1$ is optionally substituted phenyl or naphthyl;
$X^1$ is oxy, thio, sulphinyl or sulphonyl;
$Ar^2$ is optionally substituted phenylene, or a 6-membered heterocyclene moiety containing up to three nitrogen atoms;
$R^1$ is (1-6C)alkyl, (3-6C)alkenyl, (3-6C)alkynyl, cyano-(1-4C)alkyl or (2-4C)alkanoyl, or optionally substituted benzoyl; and
$R^2$ and $R^3$ together form a group of the formula —$A^2$—$X^2$—$A^3$— wherein each of $A^2$ and $A^3$ is (1-4C)alkylene and $X^2$ is oxy, thio, sulphinyl, sulphonyl or imino.

The invention also concerns processes for the manufacture of a diaryl ether heterocycle of the formula I, or a pharmaceutically-acceptable salt thereof, and pharmaceutical compositions containing said heterocycle. The compounds of the invention are inhibitors of the enzyme 5-lipoxygenase.

10 Claims, No Drawings

DIARYL ETHER HETROCYCLES

This invention concerns novel diaryl ether heterocycles and more particularly novel diaryl ether heterocycles which are inhibitors of the enzyme 5-lipoxygenase (hereinafter referred to as 5-LO). The invention also concerns processes for the manufacture of said diaryl ether heterocycles and novel pharmaceutical compositions containing said diaryl ether heterocycles. Also included in the invention is the use of said diaryl ether heterocycles in the treatment of various inflammatory and/or allergic diseases in which the direct or indirect products of 5-LO catalysed oxidation of arachidonic acid are involved, and the production of new medicaments for such use.

As stated above the diaryl ether heterocycles described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarized by G. W. Taylor and S. R. Clarke in *Trends in Pharmacological Sciences*, 1986, 7, 100–103. The leukotrienes and their metabolites have been implicated in the production and development of various inflammatory and allergic diseases such as arthritic diseases, asthma, allergic rhinitis, atopic dermatitis, psoriasis, cardiovascular and cerebrovascular disorders and inflammatory bowel disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

We have now discovered that certain diaryl ether heterocycles are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a diaryl ether heterocycle of the formula I (set out hereinafter)
wherein $Ar^1$ is phenyl or naphthyl which may optionally bear one or more substituents selected from amino, halogeno, hydroxy, cyano, (1–6C)alkyl, (2–6C)alkenyl, (2–6C)alkynyl, (1–4C)alkoxy, (1–4C)alkylthio, (1–4C)alkysulphinyl, (1–4C)alkylsulphonyl, (1–4C)alkylamino, di-[(1–4C)alkyl]amino, (1–4C)alkoxycarbonyl, (2–4C)alkanoyl, hydroxy-(1–6C)alkyl, fluoro-(1–4C)alkyl, cyano-(1–6C)alkyl, fluoro-(1–4C)alkoxy, cyano-(1–4C)alkoxy, (1–4C)alkoxy-(1–4C)alkyl, (1–4C)alkylthio-(1–4C)alkyl, (1–4C)alkylsulphinyl-(1–4C)alkyl, (1–4C)alkylsulphonyl-(1–4C)alkyl, cyano-(4–6C)cycloalkyl, (2–4C)alkanoylamino, N-[(1–4C)alkyl](2–4C)alkanoylamino, N-(2,2,2-trifluoroethyl)-(2–4C)alkanoylamino, N-[(1–4C)alkoxycarbonyl-(1–2C)alkyl]-(2–4C)alkanoylamino, trifluoroacetyl, trifluoroacetamido, N-[(1–4C)alkyl]trifluoroacetamido, 2-oxopyrrolidinyl, thia-(3–8C)alkylene, oxothia-(3–8C)alkylene, dioxothia-(3–8C)alkylene, tri-(1–4C)alkylsilyl, phenyl, benzoyl, benzamido and N-[(1–4C)alkyl]benzamido, and wherein said phenyl, benzoyl, benzamido or N-[(1–4C)alkyl]benzamido substituent may optionally bear a substituent selected from halogeno, (1–4C)alkyl and (1–4C)alkoxy;

wherein $X^1$ is oxy, thio, sulphinyl or sulphonyl;

wherein $Ar^2$ is phenylene which may optionally bear one or two substituents selected from halogeno, hydroxy, amino, nitro, cyano, carbamoyl, (1–4C)alkyl, (3–4C)alkenyloxy, (1–4C)alkoxy, (1–4C)alkylthio, (1–4C)alkylsulphinyl, (1–4C)alkysulphonyl, (1–4C)alkylamino, di-[(1–4C)alkyl]amino, fluoro-(1–4C)alkyl, cyano-(1–4C)alkyl, (1–4C)alkoxycarbonyl, N-[(1–4C)alkyl]carbamoyl, N,N-di-[(1–4C)alkyl]carbamoyl, (2–4C)alkanoylamino, fluoro-(1–4C)alkoxy, cyano(1–4C)alkoxy, carbamoyl-(1–4C)alkoxy, amino-(2–4C)alkoxy, (1–4C)alkylamino-(2–4C)alkoxy, di-[(1–4C)alkyl]amino-(2–4C)alkoxy and (1–4C)alkoxycarbonyl-(1–4C)alkoxy; or $Ar^2$ is a 6-membered heterocyclene moiety containing up to three nitrogen atoms which may optionally bear one or two substituents selected from halogeno, hydroxy, amino, cyano, (1–4C)alkyl, (1–4C)alkoxy, (1–4C)alkylamino and di-[(1–4C)alkyl]amino;

wherein $R^1$ is (1–6C)alkyl, (3–6C)alkenyl, (3–6C)alkynyl, cyano-(1–4C)alkyl or (2–4C)alkanoyl, or $R^1$ is benzoyl which may optionally bear a substituent selected from halogeno, (1–4C)alkyl and (1–4C)alkoxy; and wherein $R^2$ and $R^3$ together form a group of the formula $—A^2—X^2—A^3—$ which, together with the carbon atom to which $A^2$ and $A^3$ are attached, defines a ring having 4 to 7 ring atoms, wherein $A^2$ and $A^3$, which may be the same or different, each is (1–4C)alkylene and $X^2$ is oxy, thio, sulphinyl, sulphonyl or imino, and which ring may bear one, two or three substituents, which may be the same or different, selected from halogeno, hydroxy, cyano, (1–4C)alkyl, (1–4C)alkoxy, (1–4C)alkylthio, (1–4C)alkylsulphinyl, (1–4C)alkylsulphonyl and fluoro-(1–4C)alkyl, or which ring may bear a (1–4C)alkylenedioxy substituent;

or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of formula I defined above may exist in optically active or racemic forms by virtue of one or more substituents containing an asymmetric carbon atom, the invention includes in its definition of active ingredient any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for the number of substituents which may be present on Ar$^1$ is, for example, one, two or three.

A suitable value for a halogeno substituent which may be present on Ar$^1$, Ar$^2$, R$^1$ or on a phenyl, benzoyl, benzamido or N-[(1-4C)alkyl]benzamido substituent on Ar$^1$ is, for example, fluoro, chloro, bromo or iodo.

A suitable value for a (1-6C)alkyl substituent which may be present on Ar$^1$ is, for example, methyl, ethyl, propyl, isopropyl, butyl, isobutyl, sec-butyl, tert-butyl, pentyl, isopentyl, hexyl or isohexyl.

A suitable value for a (1-4C)alkyl substituent which may be present on Ar$^2$, R$^1$ or on a phenyl, benzoyl, benzamido or N-[(1-4C)alkyl]benzamido substituent on Ar$^1$ is, for example, methyl, ethyl, propyl, isopropyl, butyl, isobutyl or sec-butyl.

A suitable value for a (2-6C)alkenyl substituent on Ar$^1$ is, for example, vinyl, allyl, 2-butenyl or 3-butenyl.

A suitable value for a (2-6C)alkynyl substituent on Ar$^1$ is, for example, ethynyl, 1-propynyl, 2-propynyl, 1-butynyl or 2-butynyl.

A suitable value for a (1-4C)alkoxy substituent which may be present on Ar$^1$, Ar$^2$, R$^1$ or on a phenyl, benzoyl, benzamido or N-[(1-4C)alkyl]benzamido substituent on Ar$^1$ is, for example, methoxy, ethoxy, propoxy, isopropoxy or butoxy.

A suitable value for a (2-4C)alkanoyl substituent which may be present on Ar$^1$ or for R$^1$ when it is (2-4C)alkanoyl is, for example, acetyl, propionyl, butyryl or isobutyryl.

Suitable values for substituents which may be present on Ar$^1$ or Ar$^2$ include, for example:

| | |
|---|---|
| for (1-4C)alkylthio: | methylthio, ethylthio, propylthio, isopropylthio and butylthio; |
| for (1-4C)alkylsulphinyl: | methylsulphinyl, ethylsulphinyl, propylsulphinyl, isopropylsulphinyl and butylsulphinyl; |
| for (1-4C)alkylsulphonyl: | methylsulphonyl, ethylsulphonyl, propylsulphonyl, isopropylsulphonyl and butylsulphonyl; |
| for (1-4C)alkylamino: | methylamino, ethylamino, propylamino and butylamino; |
| for di-[(1-4C)alkyl]amino: | dimethylamino, diethylamino and dipropylamino; |
| for (1-4C)alkoxycarbonyl: | methoxycarbonyl, ethoxycarbonyl and tert-butoxycarbonyl; |
| for fluoro-(1-4C)alkyl: | fluoromethyl, difluoromethyl, trifluoromethyl, 2-fluoroethyl, 2,2,2-trifluoroethyl and pentafluoroethyl; |
| for fluoro-(1-4C)alkoxy: | trifluoromethoxy, 2,2,2-trifluoroethoxy and pentafluoroethoxy; |
| for cyano-(1-4C)alkoxy: | cyanomethoxy, 2-cyanoethoxy and 3-cyanopropoxy; |
| for (2-4C)alkanoylamino: | acetamido, propionamido and butyramido. |

Suitable values for substituents which may be present on Ar$^1$ include, for example:

| | |
|---|---|
| for hydroxy-(1-6C)alkyl: | hydroxymethyl, 1-hydroxyethyl, 2-hydroxyethyl, 1-hydroxypropyl, 2-hydroxypropyl, 2-hydroxyprop-2-yl, 3-hydroxypropyl, 2-hydroxybut-2-yl and 3-hydroxypent-3-yl; |
| for cyano-(1-6C)alkyl: | cyanomethyl, 1-cyanoethyl, 2-cyanoethyl, 3-cyanopropyl, 2-cyanoprop-2-yl, 2-cyanobut-2-yl and 3-cyanopent-3-yl; |
| for (1-4C)alkoxy-(1-4C)alkyl: | methoxymethyl, 1-methoxyethyl, 2-methoxyethyl, 2-methoxyprop-2-yl, 2-methoxybut-2-yl, ethoxymethyl, 1-ethoxyethyl, 2-ethoxyethyl, 2-ethoxyprop-2-yl and 2-ethoxybut-2-yl; |
| for (1-4C)alkylthio-(1-4C)alkyl: | methylthiomethyl, 1-methylthioethyl, 2-methylthioethyl, 2-methylthioprop-2-yl, ethylthiomethyl, 1-ethylthioethyl, 2-ethylthioethyl and 2-ethylthioprop-2-yl; |
| for (1-4C)alkylsulphinyl-(1-4C)alkyl: | methylsulphinylmethyl, 1-methylsulphinylethyl, 2-methylsulphinylethyl, 2-methylsulphinylprop-2-yl, ethylsulphinylmethyl, 1-ethylsulphinylethyl, 2-ethylsulphinylethyl and 2-ethylsulphinylprop-2-yl; |
| for (1-4C)alkylsulphonyl-(1-4C)alkyl: | methylsulphonylmethyl, 1-methylsulphonylethyl, 2-methylsulphonylethyl, 2-methylsulphonylprop-2-yl, ethylsulphonylmethyl, 1-ethylsulphonylethyl, 2-ethylsulphonylethyl and 2-ethylsulphonylprop-2-yl; |
| for cyano-(3-6C)cycloalkyl: | 1-cyanocyclopropyl, 1-cyanocyclobutyl, 1-cyanocyclopentyl and 1-cyanocyclohexyl; |
| for N-[(1-4C)alkyl]-(2-4C)alkanoylamino: | N-methylacetamido, N-methylpropionamido, N-methylbutyramido, N-ethylacetamido, N-ethylpropionamido and N-ethylbutyramido; |
| for N-(2,2,2-trifluoroethyl)-(2-4C)alkanoylamino: | N-(2,2,2-trifluoroethyl)acetamido and N-(2,2,2-trifluoroethyl)propionamido; |
| for N-[(1-4C)alkoxycarbonyl-(1-2C)alkyl]-(2-4C)alkanoylamino: | N-(methoxycarbonylmethyl)acetamido, N-(ethoxycarbonylmethyl)acetamido, N-[2-(methoxycarbonyl)ethyl]acetamido, N-(methoxycarbonylmethyl)propionamido and N-(ethoxycarbonylmethyl)propionamido; |
| for N-[(1-4C)alkyl]-trifluoroacetamido: | N-methyltrifluoroacetamido and N-ethyltrifluoroacetamido; |
| for 2-oxopyrrolidinyl: | 2-oxopyrrolidin-1-yl, 2-oxopyrrolidin-3-yl, 2-oxopyrrolidin-4-yl and 2-oxopyrrolidin-5-yl; |
| for thia-(3-8C)alkylene: | 2-thiatrimethylene, 1,3-dimethyl-2-thiatrimethylene and 1,1,3,3-tetramethyl-2-thiatrimethylene; |
| for oxothia-(3-8C)alkylene: | 2-oxo-2-thiatrimethylene, 1,3-dimethyl-2-oxo-2-thiatrimethylene and 1,1,3,3-tetramethyl-2-oxo-2-thiatrimethylene; |
| for dioxothia-(3-8C)alkylene: | 2,2-dioxo-2-thiatrimethylene, 1,3-dimethyl-2,2-dioxo-2-thiatrimethylene and 1,1,3,3-tetramethyl-2,2-dioxo-2-thiatrimethylene; |
| for tri-(1-4C)alkylsilyl: | trimethylsilyl, triethylsilyl and tripropylsilyl; |
| for N-[(1-4C)alkyl]-benzamido: | N-methylbenzamido and N-ethylbenzamido. |

A suitable value for Ar$^2$ when it is phenylene is, for example, 1,3-phenylene or 1,4-phenylene.

A suitable value for Ar$^2$ when it is a 6-membered heterocyclene moiety containing up to three nitrogen atoms is, for example, pyridylene, pyrimidinylene, pyridazinylene, pyrazinylene or 1,3,5-triazinylene. Conveniently Ar$^2$ when it is a 6-membered heterocyclene moiety containing up to three nitrogen atoms is, for example, 2,4-, 2,5-, 3,5- or 2,6-pyridylene, 2,4-, 2,5- or 4,6-pyrimidinylene, 3,5- or 3,6-pyridazinylene or 2,5- or 2,6-pyrazinylene.

Suitable values for substituents which may be present on $Ar^2$ include, for example:

| | |
|---|---|
| for (3–4C)alkenyloxy: | allyloxy, methylallyoxy, but-2-enyloxy and but-3-enyloxy; |
| for cyano-(1–4C)alkyl: | cyanomethyl, 1-cyanoethyl, 2-cyanoethyl, 3-cyanopropyl and 2-cyanoprop-2-yl; |
| for N-[(1–4C)alkyl]-carbamoyl: | N-methylcarbamoyl, N-ethylcarbamoyl and N-propylcarbamoyl; |
| for N,N-di-[(1–4C)alkyl]-carbamoyl: | N,N-dimethylcarbamoyl and N,N-diethylcarbamoyl; |
| for carbamoyl-(1–4C)-alkoxy: | carbamoylmethoxy, 2-carbamoylethoxy and 3-carbamoylpropoxy; |
| for amino-(2–4C)alkoxy: | 2-aminoethoxy, 3-aminopropoxy and 4-aminobutoxy; |
| for (1–4C)alkylamino-(2–4C)alkoxy: | 2-methylaminoethoxy, 3-methylaminopropoxy and 2-ethylaminoethoxy; |
| for di-[(1–4C)alkyl]amino-(2–4C)alkoxy: | 2-dimethylaminoethoxy, 3-dimethylaminopropoxy and 2-diethylaminoethoxy; |
| for (1–4C)alkoxycarbonyl-(1–4C)alkoxy: | methoxycarbonylmethoxy, 2-methoxycarbonylethoxy, ethoxycarbonylmethoxy and 2-ethoxycarbonylethoxy. |

A suitable value for $R^1$ when it is (1–6C)alkyl is, for example, methyl, ethyl, propyl, butyl, pentyl or hexyl.

A suitable value for $R^1$ when it is (3–6C)alkenyl is, for example, allyl, 2-butenyl or 3-butenyl; and when it is (3–6C)alkynyl is, for example, 2-propynyl or 2-butynyl.

A suitable value for $R^1$ when it is cyano-(1–4C)alkyl is, for example, cyanomethyl, 2-cyanoethyl or 3-cyanopropyl.

When $R^2$ and $R^3$ together form a group of the formula $-A^2-X^2-A^3-$ which, together with the carbon atom to which $A^2$ and $A^3$ are attached, defines a ring having 4 to 7 ring atoms then a suitable value for $A^2$ or $A^3$, which may be the same or different, when each is (1–4C)alkylene is, for example, methylene, ethylene, trimethylene or tetramethylene.

Suitable values for the one, two or three substituents which may be present on said 4- to 7-membered ring include, for example:

| | |
|---|---|
| for halogeno: | fluoro, chloro and bromo; |
| for (1–4C)alkyl: | methyl, ethyl, propyl, isopropyl and butyl; |
| for (1–4C)alkoxy: | methoxy, ethoxy, propoxy, isopropoxy and butoxy; |
| for (1–4C)alkylthio: | methylthio, ethylthio, propylthio, isopropylthio and butylthio; |
| for (1–4C)alkylsulphinyl: | methylsulphinyl, ethylsulphinyl, propylsulphinyl, isopropylsulphinyl and butylsulphinyl; |
| for (1–4C)alkylsulphonyl: | methylsulphonyl, ethylsulphonyl, propylsulphonyl, isopropylsulphonyl and butylsulphonyl; |
| for fluoro-(1–4C)alkyl: | fluoromethyl, difluoromethyl, trifluoromethyl, 2-fluoroethyl, 2,2,2-trifluoroethyl and pentafluoroethyl; |
| for (1–4C)alkylenedioxy: | methylenedioxy and ethylenedioxy. |

A suitable pharmaceutically-acceptable salt of a diaryl ether heterocycle of the invention is, for example, an acid-addition salt of a diaryl ether heterocycle of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a diaryl ether heterocycle of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention are, for example, diaryl ether heterocycles of the formula I wherein:

(a) $Ar^1$ is phenyl, naphth-1-yl or naphth-2-yl which may optionally bear one, two or three substituents selected from amino, fluoro, chloro, bromo, iodo, cyano, methyl, ethyl, isopropyl, tert-butyl, methoxy, methylthio, methylsulphinyl, methylsulphonyl, methoxycarbonyl, difluoromethyl, trifluoromethyl, 1-cyanoethyl, 2-cyanoethyl, 2-cyanoprop-2-yl and cyanomethoxy; and $X^1$, $Ar^2$, $R^1$, $R^2$ and $R^3$ have any of the meanings defined hereinbefore;

(b) $Ar^1$ is phenyl or naphth-2-yl which may optionally bear one or two substituents selected from fluoro, chloro, bromo, methyl, ethyl, isopropyl, tert-butyl, methoxy, ethoxy, isopropoxy, methylthio, methylsulphinyl, methylsulphonyl, acetyl, propionyl, isobutyryl, hydroxymethyl, 1-hydroxyethyl, 2-hydroxyethyl, 1-hydroxypropyl, 2-hydroxyprop-2-yl, 3-hydroxypent-3-yl, difluoromethyl, trifluoromethyl, cyanomethyl, 1-cyanoethyl, 2-cyanoethyl, 2-cyanoprop-2-yl, 3-cyanopent-3-yl, trifluoromethoxy, 2,2,2-trifluoroethoxy, methoxymethyl, 1-methoxyethyl, 2-methoxyethyl, 2-methoxyprop-2-yl, methylthiomethyl, 1-methylthioethyl, 2-methylthioethyl, 2-methylthioprop-2-yl, methylsulphinylmethyl, 1-methylsulphinylethyl, 2-methylsulphinylethyl, 2-methylsulphinylprop-2-yl, methylsulphonylmethyl, 1-methylsulphonylethyl, 2-methylsulphonylethyl, 2-methylsulphonylprop-2-yl, 1-cyanocyclopentyl, 1-cyanocyclohexyl, acetamido, propionamido, N-methylacetamido, N-methylpropionamido, trifluoroacetyl, trifluoroacetamido, N-methyltrifluoroacetamido, 2-oxopyrrolidin-1-yl, 1,1,3,3-tetramethyl-2,2-dioxo-2-thiatrimethylene, trimethylsilyl and phenyl; and $X^1$, $Ar^2$, $R^1$, $R^2$ and $R^3$ have any of the meanings defined hereinbefore;

(c) $Ar^1$ is phenyl or naphth-2-yl which may optionally bear one or two substituents selected from amino, fluoro, chloro, bromo, methyl, ethyl, isopropyl, tert-butyl, methoxy, ethoxy, isopropoxy, methylthio, methylsulphinyl, methylsulphonyl, methylamino, dimethylamino, acetyl, propionyl, isobutyryl, hydroxymethyl, 1-hydroxyethyl, 2-hydroxyethyl, 1-hydroxypropyl, 2-hydroxyprop-2-yl, 3-hydroxypent-3-yl, difluoromethyl, trifluoromethyl, cyanomethyl, 1-cyanoethyl, 2-cyanoethyl, 2-cyanoprop-2-yl, 3-cyanopent-3-yl, trifluoromethoxy, 2,2,2-trifluoroethoxy, methoxymethyl, 1-methoxyethyl, 2-methoxyethyl, 2-methoxyprop-2-yl, methylthiomethyl, 1-methylthioethyl, 2-methylthioethyl, 2-methylthioprop-2-yl, methylsulphinylmethyl, 1-methylsulphinylethyl, 2-methylsulphinylethyl, 2-methylsulphinylprop-2-yl, methylsulphonylmethyl, 1-methylsulphonylethyl, 2-methylsulphonylethyl, 2-methylsulphonylprop-2-yl, 1-cyanocyclopentyl, 1-cyanocyclohexyl, acetamido, propionamido, N-methylacetamido, N-methylpropionamido, N-(2,2,2-trifluoroethyl)acetamido, N-(methoxycarbonylmethyl)acetamido, N-(ethoxycarbonylmethyl)acetamido, trifluoroacetyl, trifluoroacetamido, N-methyltrifluoroacetamido, 2-oxopyrrolidin-1-yl, 1,1,3,3-tetramethyl-2,2-dioxo-2-thiatrimethylene, trimethylsilyl, phenyl, benzoyl, benzamido and N-methylbenzamido, and wherein said phenyl, benzoyl, benzamido or N-methylbenzamido substituent may optionally bear a substituent selected from fluoro, chloro, methyl and methoxy; and $X^1$, $Ar^2$, $R^1$, $R^2$ and $R^3$ have any of the meanings defined hereinbefore;

(d) $X^1$ is thio, sulphinyl or sulphonyl; and $Ar^1$, $Ar^2$, $R^1$, $R^2$ and $R^3$ have any of the meanings defined hereinbefore;

(e) $Ar^2$ is 1,3-phenylene or 1,4-phenylene which may optionally bear one substituent selected from fluoro, chloro, hydroxy, amino, nitro, methyl, methoxy, methylthio, methylsulphinyl, methylsulphonyl, methylamino, dimethylamino, trifluoromethyl, acetamido, cyanomethoxy and carbamoylmethoxy; and $Ar^1$, $X^1$, $R^1$, $R^2$ and $R^3$ have any of the meanings defined hereinbefore;

(f) $Ar^2$ is 1,3-phenylene or 1,4-phenylene which may optionally bear one or two substituents selected from fluoro, chloro, bromo, amino, nitro, cyano, methyl, methoxy, methylamino, dimethylamino and trifluoromethyl; and $Ar^1$, $X^1$, $R^1$, $R^2$ and $R^3$ have any of the meanings defined hereinbefore;

(g) $Ar^2$ is 2,4-, 2,5-, 3,5- or 2,6-pyridylene or 4,6-pyrimidylene which may optionally bear one substituent selected from chloro, methyl and methoxy; and $Ar^1$, $X^1$, $R^1$, $R^2$ and $R^3$ have any of the meanings defined hereinbefore;

(h) $Ar^2$ is 3,5-pyridylene; and $Ar^1$, $X^1$, $R^1$, $R^2$ and $R^3$ have any of the meanings defined hereinbefore;

(i) $R^1$ is methyl, ethyl, allyl, 2-propynyl or cyanomethyl; and $Ar^1$, $X^1$, $Ar^2$, $R^2$ and $R^3$ have any of the meanings defined hereinbefore;

(j) $R^1$ is methyl, ethyl, allyl or 2-propynyl; and $Ar^1$, $X^1$, $Ar^2$, $R^2$ and $R^3$ have any of the meanings defined hereinbefore; or (k) $R^2$ and $R^3$ together form a group of the formula —$A^2$—$X^2$—$A^3$— which, together with the carbon atom to which $A^2$ and $A^3$ are attached, defines a ring having 4 to 7 ring atoms, wherein $A^2$ and $A^3$, which may be the same or different, each is methylene, ethylene, trimethylene or tetramethylene and $X^2$ is oxy, thio, sulphinyl or sulphonyl, and which ring may bear a substituent selected from fluoro, hydroxy, methyl, methoxy, ethoxy, methylthio, methylsulphinyl, methylsulphonyl, trifluoromethyl and methylenedioxy; and $Ar^1$, $X^1$, $Ar^2$ and $R^1$ have any of the meanings defined hereinbefore;

(l) $R^2$ and $R^3$ together form a group of the formula —$A^2$—$X^2$—$A^3$— which, together with the carbon atom to which $A^2$ and $A^3$ are attached, defines a ring having 4 to 7 ring atoms, wherein $A^2$ and $A^3$, which may be the same or different, each is methylene or ethylene and $X^2$ is oxy, and which ring may bear one or two substituents selected from fluoro, hydroxy, methyl, ethyl, propyl, methoxy and trifluoromethyl; and $Ar^1$, $X^1$, $Ar^2$ and $R^1$ have any of the meanings defined hereinbefore; or a pharmaceutically-acceptable salt thereof.

A preferred compound of the invention comprises a diaryl ether heterocycle of the formula I wherein $Ar^1$ is phenyl, naphth-1-yl or naphth-2-yl which may optionally bear one or two substituents selected from amino, fluoro, chloro, cyano, methyl, tert-butyl, methoxy, methylthio, methylsulphinyl, methylsulphonyl and 2-cyanoprop-2-yl;

$X^1$ is thio, sulphinyl or sulphonyl;

$Ar^2$ is 1,3-phenylene or 1,4-phenylene which may optionally bear one substituent selected from fluoro, hydroxy, amino, nitro, methoxy, methylamino, cyanomethoxy and trifluoromethyl; or $Ar^2$ is 3,5-pyridylene;

$R^1$ is methyl or ethyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy or thio, and which ring may bear a substituent selected from fluoro, methyl, methoxy and trifluoromethyl;

or a pharmaceutically-acceptable salt thereof.

A further preferred compound of the invention comprises a diaryl ether heterocycle of the formula I wherein $Ar^1$ is phenyl or naphth-2-yl which may optionally bear one or two substituents selected from fluoro, chloro, bromo, methyl, ethyl, isopropyl, tert-butyl, methoxy, ethoxy, isopropoxy, methylthio, methylsulphinyl, methylsulphonyl, acetyl, propionyl, isobutyryl, hydroxymethyl, 1-hydroxyethyl, 2-hydroxyethyl, 1-hydroxypropyl, 2-hydroxyprop-2-yl, 3-hydroxypent-3-yl, difluoromethyl, trifluoromethyl, cyanomethyl, 1-cyanoethyl, 2-cyanoethyl, 2-cyanoprop-2-yl, 3-cyanopent-3-yl, trifluoromethoxy, 2,2,2-trifluoroethoxy, methoxymethyl, 1-methoxyethyl, 2-methoxyethyl, 2-methoxyprop-2-yl, methylthiomethyl, 1-methylthioethyl, 2-methylthioethyl, 2-methylthioprop-2-yl, methylsulphinylmethyl, 1-methylsulphinylethyl, 2-methylsulphinylethyl, 2-methylsulphinylprop-2-yl, methylsulphonylmethyl, 1-methylsulphonylethyl, 2-methylsulphonylethyl, 2-methylsulphonylprop-2-yl, 1-cyanocyclopentyl, 1-cyanocyclohexyl, acetamido, propionamido, N-methylacetamido, N-methylpropionamido, trifluoroacetyl, trifluoroacetamido, N-methyltrifluoroacetamido, 2-oxopyrrolidin-1-yl, 1,1,3,3-tetramethyl-2,2-dioxo-2-thiatrimethylene, trimethylsilyl and phenyl;

$X^1$ is oxy, thio, sulphinyl or sulphonyl;

$Ar^2$ is 1,3-phenylene or 1,4-phenylene which may optionally bear one or two substituents selected from fluoro, chloro, bromo, amino, nitro, cyano, methyl, methoxy, methylamino, dimethylamino and trifluoromethyl, or $Ar^2$ is 3,5-pyridylene;

$R^1$ is methyl, ethyl, allyl or 2-propynyl; and $R^2$ and $R^3$ together form a group of the formula —$A^2$—$X^2$—$A^3$— which, together with the carbon atom to which $A^2$ and $A^3$ are attached, defines a ring having 4 to 7 ring atoms, wherein $A^2$ and $A^3$, which may be the same or different, each is methylene or ethylene and $X^2$ is oxy, and which ring may bear one or two substituents selected from fluoro, hydroxy, methyl, ethyl, propyl, methoxy and trifluoromethyl;

or a pharmaceutically-acceptable salt thereof.

A further preferred compound of the invention comprises a diaryl ether heterocycle of the formula I wherein $Ar^1$ is phenyl or naphth-2-yl which may optionally bear one or two substituents selected from amino, fluoro, chloro, bromo, methyl, ethyl, isopropyl, tert-butyl, methoxy, ethoxy, isopropoxy, methylthio, methylsulphinyl, methylsulphonyl, methylamino, dimethylamino, acetyl, propionyl, isobutyryl, hydroxymethyl, 1-hydroxyethyl, 2-hydroxyethyl, 1-hydroxypropyl, 2-hydroxyprop-2-yl, 3-hydroxypent-3-yl, difluoromethyl, trifluoromethyl, cyanomethyl, 1-cyanoethyl, 2-cyanoethyl, 2-cyanoprop-2-yl, 3-cyanopent-3-yl, trifluoromethoxy, 2,2,2-trifluoroethoxy, methoxymethyl, 1-methoxyethyl, 2-methoxyethyl, 2-methoxyprop-2-yl, methylthiomethyl, 1-methylthioethyl, 2-methylthioethyl, 2-methylthioprop-2-yl, methylsulphinylmethyl, 1-methylsulphinylethyl, 2-methylsulphinylethyl, 2-methylsulphinylprop-2-yl, methylsulphonylmethyl, 1-methylsulphonylethyl, 2-methylsulphonylethyl, 2-methylsulphonylprop-2-yl, 1-cyanocyclopentyl, 1-cyanocyclohexyl, acetamido, propionamido, N-methylacetamido, N-methylpropionamido, N-(2,2,2-trifluoroethyl)acetamido, N-(methoxycarbonylmethyl)acetamido, N-(ethoxycarbonylmethyl)acetamido, trifluoroacetyl, trifluoroacetamido, N-methyltrifluoroacetamido, 2-oxopyrrolidin-1-yl, 1,1,3,3-tetramethyl-2,2-dioxo-2-thiatrimethylene, trimethylsilyl, phenyl, benzoyl, benzamido and N-methylbenzamido, and wherein said phenyl, benzoyl, benzamido or N-methylbenzamido substituent may optionally bear a substituent selected from fluoro, chloro, methyl and methoxy;

$X^1$ is oxy, thio, sulphinyl or sulphonyl;

$Ar^2$ is 1,3-phenylene or 1,4-phenylene which may optionally bear one or two substituents selected from fluoro, chloro, bromo, amino, nitro, cyano, methyl, methoxy, methylamino, dimethylamino and trifluoromethyl, or $Ar^2$ is 3,5-pyridylene;

$R^1$ is methyl, ethyl, allyl or 2-propynyl; and $R^2$ and $R^3$ together form a group of the formula —$A^2$—$X^2$—$A^3$— which, together with the carbon atom to which $A^2$ and $A^3$ are attached, defines a ring having 4 to 7 ring atoms, wherein $A^2$ and $A^3$, which may be the same or different, each is methylene or ethylene and $X^2$ is oxy, and which ring may bear one or two substituents selected from fluoro, hydroxy, methyl, ethyl, propyl, methoxy and trifluoromethyl;

or a pharmaceutically-acceptable salt thereof.

A further preferred compound of the invention comprises a diaryl ether heterocycle of the formula I wherein $Ar^1$ is phenyl which may optionally bear one or two substituents selected from fluoro, chloro, methyl, t-butyl, methylthio, methylsulphinyl and 2-cyanoprop-2-yl; or $Ar^1$ is naphth-2-yl which may optionally bear a fluoro substituent;

$X^1$ is thio, sulphinyl or sulphonyl;

$Ar^2$ is 1,3-phenylene which may optionally bear one substituent selected from fluoro, amino, nitro, methoxy and trifluoromethyl; or $Ar^2$ is 3,5-pyridylene;

$R^1$ is methyl or ethyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene and $X^2$ is oxy, and which ring may bear a substituent selected from methyl and methoxy;

or a pharmaceutically-acceptable salt thereof.

A further preferred compound of the invention comprises a diaryl ether heterocycle of the formula I wherein $Ar^1$ is phenyl which may optionally bear one or two substituents selected from chloro, isopropyl, tert-butyl, isopropoxy, isobutyryl, 2-hydroxyprop-2-yl, 2-cyanoprop-2-yl, 3-cyanopent-3-yl, 2,2,2-trifluoroethoxy, 2-methoxyprop-2-yl, 1-cyanocyclopentyl, acetamido, N-methylacetamido, 1,1,3,3-tetramethyl-2,2-dioxo-2-thiatrimethylene, trimethylsilyl and phenyl; or $Ar^1$ is naphth-2-yl which may optionally bear a substituent selected from fluoro, methyl and trifluoromethyl;

$X^1$ is oxy, thio, sulphinyl or sulphonyl;

$Ar^2$ is 1,3-phenylene which may optionally bear one or two substituents selected from fluoro, chloro, bromo, amino, nitro, cyano, methoxy and trifluoromethyl;

$R^1$ is methyl, ethyl or allyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy, and which ring may bear one or two substituents selected from methyl, ethyl and methoxy;

or a pharmaceutically-acceptable salt thereof.

A further preferred compound of the invention comprises a diaryl ether heterocycle of the formula I wherein $Ar^1$ is phenyl which may optionally bear one or two substituents selected from chloro, isopropyl, tert-butyl, isopropoxy, dimethylamino, acetyl, isobutyryl, 2-hydroxyprop-2-yl, 2-cyanoprop-2-yl, 3-cyanopent-3-yl, 2,2,2-trifluoroethoxy, 2-methoxyprop-2-yl, 1-cyanocyclopentyl, acetamido, N-methylacetamido, propionamido, N-methylpropionamido, N-(methoxycarbonylmethyl)acetamido, trifluoroacetyl, N-methyltrifluoroacetamido, 2-oxopyrrolidin-1-yl, 1,1,3,3-tetramethyl2,2-dioxo-2-thiatrimethylene, trimethylsilyl, phenyl, benzoyl, 4-chlorobenzoyl and N-methylbenzamido; or $Ar^1$ is naphth-2-yl which may optionally bear a substituent selected from fluoro, methyl and trifluoromethyl;

$X^1$ is oxy, thio, sulphinyl or sulphonyl;

$Ar^2$ is 1,3-phenylene which may optionally bear one or two substituents selected from fluoro, chloro, bromo, amino, nitro, cyano, methoxy and trifluoromethyl;

$R^1$ is methyl, ethyl or allyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy, and which ring may bear one or two substituents selected from methyl, ethyl and methoxy;

or a pharmaceutically-acceptable salt thereof.

A further preferred compound of the invention comprises a diaryl ether heterocycle of the formula I wherein $Ar^1$ is 4-t-butylphenyl, 4-(2-cyanoprop-2-yl)phenyl or naphth-2-yl;

$X^1$ is thio;

Ar$^2$ is 1,3-phenylene, 5-fluoro-1,3-phenylene or 5-trifluoromethyl-1,3-phenylene;

R$^1$ is methyl; and

R$^2$ and R$^3$ together form a group of the formula —A$^2$—X$^2$—A$^3$— which, together with the carbon atom to which A$^2$ and A$^3$ are attached, defines a ring having 6 ring atoms, wherein each of A$^2$ and A$^3$ is ethylene and X$^2$ is oxy and which ring may bear a methyl substituent alpha to X$^2$;

or a pharmaceutically-acceptable salt thereof.

A further preferred compound of the invention comprises a diaryl ether heterocycle of the formula I wherein Ar$^1$ is 4-t-butylphenyl, 3-(2-cyanoprop-2-yl)phenyl, 4-(2-cyanoprop-2-yl)phenyl, 3-chloro-4-(2-cyanoprop-2-yl)phenyl, 4-(1-cyanocyclopentyl)phenyl, 4-trimethylsilylphenyl, 3-biphenylyl, 4-biphenylyl or naphth-2-yl;

X$^1$ is oxy, thio or sulphonyl;

Ar$^2$ is 1,3-phenylene, 5-fluoro-1,3-phenylene, 2,5-difluoro-1,3-phenylene, 5-bromo-1,3-phenylene or 5-trifluoromethyl-1,3-phenylene;

R$^1$ is methyl or allyl; and

R$^2$ and R$^3$ together form a group of the formula —A$^2$—X$^2$—A$^3$— which, together with the carbon atom to which A$^2$ and A$^3$ are attached, defines a ring having 6 ring atoms, wherein each of A$^2$ and A$^3$ is ethylene and X$^2$ is oxy and which ring may bear a methyl substituent alpha to X$^2$;

or a pharmaceutically-acceptable salt thereof.

A further preferred compound of the invention comprises a diaryl ether heterocycle of the formula I wherein Ar$^1$ is 4-t-butylphenyl, 3-(2-cyanoprop-2-yl)phenyl, 4-(2-cyanoprop-2-yl)phenyl, 3-chloro-4-(2-cyanoprop-2-yl)phenyl, 4-(1-cyanocyclopentyl)phenyl, 1,1,3,3-tetramethyl-1,3-dihydrobenzo[c]thien-5-yl, 4-trimethylsilylphenyl, 3-biphenylyl, 4-biphenylyl, 4-benzoylphenyl or naphth-2-yl;

X$^1$ is oxy, thio or sulphonyl;

Ar$^2$ is 1,3-phenylene, 5-fluoro-1,3-phenylene, 2,5-difluoro-1,3-phenylene, 5-bromo-1,3-phenylene or 5-trifluoromethyl-1,3-phenylene;

R$^1$ is methyl or allyl; and

R$^2$ and R$^3$ together form a group of the formula —A$^2$—X$^2$—A$^3$— which, together with the carbon atom to which A$^2$ and A$^3$ are attached, defines a ring having 6 ring atoms, wherein each of A$^2$ and A$^3$ is ethylene and X$^2$ is oxy and which ring may bear a methyl substituent alpha to X$^2$;

or a pharmaceutically-acceptable salt thereof.

Specific especially preferred compounds of the invention include, for example, the following diaryl ether derivatives of the formula I, or pharmaceutically-acceptable salts thereof:

4-methoxy-4-[3-(naphth-2-ylthio)phenyl]tetrahydropyran,

4-[3-(4-t-butylphenylthio)phenyl]-4-methoxytetrahydropyran, 4-methoxy-4-[3-(naphth-2-ylthio)-5-trifluoromethylphenyl]tetrahydropyran and 4-[3-(4-(2-cyanoprop-2-yl)phenylthio)-5-trifluoromethylphenyl]-4-methoxytetrahydropyran.

Further specific especially preferred compounds of the invention include, for example, the following diaryl ether derivatives of the formula I, or pharmaceutically-acceptable salts thereof:

4-allyloxy-4-[2,5-difluoro-3-(naphth-2-ylthio)phenyl]tetrahydropyran, (2RS,4SR)-4-[3-(4-tert-butylphenylthio)phenyl]-4-methoxy-2-methyltetrahydropyran, (2RS,4SR)-4-allyloxy-4-[5-fluoro-3-(4-tert-butylphenoxy)phenyl]-2-methyltetrahydropyran, 4-[3-(3-chloro-4-(2-cyanoprop-2-yl)phenylthio)phenyl]-4-methoxytetrahydropyran, (2S,4R)-4-[3-(4-tert-butylphenylthio)phenyl]-4-methoxy-2-methyltetrahydropyran and (2S,4R)-4-[5-fluoro-3-(4-tert-butylphenylthio)phenyl]-4-methoxy-2-methyltetrahydropyran.

A compound of the invention comprising a diaryl ether heterocycle of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, Ar$^1$, X$^1$, Ar$^2$, R$^1$, R$^2$ and R$^3$ have any of the meanings defined hereinbefore.

(a) The coupling, in the presence of a suitable base, of a compound of the formula Ar$^1$—X$^1$—H with a compound of the formula II wherein Z is a displaceable group; provided that, when there is an amino, imino, alkylamino or hydroxy group in Ar$^1$, Ar$^2$, R$^2$ or R$^3$ any amino, imino, alkylamino or hydroxy group may be protected by a conventional protecting group or alternatively any such group need not be protected; whereafter any undesired protecting group in Ar$^1$, Ar$^2$, R$^2$ or R$^3$ is removed by conventional means.

A suitable displaceable group Z is, for example, a halogeno or sulphonyloxy group, for example a chloro, bromo, iodo, methanesulphonyloxy or toluene-p-sulphonyloxy group.

A suitable base for the coupling reaction is, for example, an alkali or alkaline earth metal carbonate, (1–4C)alkoxide, hydroxide or hydride, for example sodium carbonate, potassium carbonate, sodium ethoxide, sodium butoxide, sodium hydroxide, potassium hydroxide, sodium hydride or potassium hydride. The coupling reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, 10° to 150° C., conveniently in the range 70° to 150° C.

Conveniently the reaction may be performed in the presence of a suitable catalyst, for example a metallic catalyst, for example palladium(O) or copper(I) such as tetrakis(triphenylphosphine)palladium, cuprous chloride or cuprous bromide.

A suitable protecting group for an amino, imino or alkylamino group is, for example, an acyl group for example a (2–4C)alkanoyl group (especially acetyl), a (1–4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a hydroxy group is, for example, an acyl group, for example a (2–4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formula $Ar^1$—$X^1$—H and of the formula II may be obtained by standard procedures of organic chemistry. The preparation of examples of such starting materials is described within the accompanying non-limiting Examples which are provided for the purpose of illustration only. Other necessary starting materials are obtainable by analogous procedures to those described or by modifications thereto which are within the ordinary skill of an organic chemist.

Conveniently intermediates of the formula II wherein Z, $Ar^2$, $R^1$, $R^2$ and $R^3$ have the meanings defined hereinbefore, may be obtained by way of compounds of the formula Z—$Ar^2$—Y, wherein Z and $Ar^2$ have the meanings defined hereinbefore and Y is, for example, a halogeno, formyl, alkanoyl, nitrile or alkoxycarbonyl group, as illustrated in accompanying Scheme I (set out hereinafter). Thus, for example, in the accompanying non-limiting Examples it is shown how to convert a compound of the formula Z—Ar—Y wherein Y is a halogeno group to a compound of the formula II.

It will also be appreciated that the intermediate of the formula II may conveniently be obtained from the compound of the formula Z—$Ar^2$—Y, as defined hereinbefore, by reversing the order of introduction of the groups $R^2$ and $R^3$ which is used in Scheme I.

(b) The coupling, in the presence of a suitable base as defined hereinbefore, of a compound of the formula III with a compound of the formula $Ar^1$—Z wherein Z is a displaceable group as defined hereinbefore; provided that, when there is an amino, imino, alkylamino or hydroxy group in $Ar^1$, $Ar^2$, $R^1$, $R^2$ or $R^3$, any amino, imino, alkylamino or hydroxy group may be protected by a conventional protecting group as defined hereinbefore or alternatively any such group need not be protected; whereafter any desired protecting group in $Ar^1$, $Ar^2$, $R^1$, $R^2$ or $R^3$ is removed by conventional means.

The coupling reaction is conveniently performed in a suitable inert solvent as defined hereinbefore and at a temperature in the range, for example, 10° to 200° C., conveniently in the range 70° to 150° C. The reaction may conveniently be performed in the presence of a suitable catalyst as defined hereinbefore.

The starting materials of the formula $Ar^1$—Z and of the formula III may be obtained by standard procedures of organic chemistry. The preparation of such starting materials is described within the accompanying non-limiting Examples which are provided for the purpose of illustration only. Alternatively necessary starting materials are obtainable by analogous procedures to those illustrated in accompanying Scheme II (set out hereinafter) or by modifications thereto which are within the ordinary skill of an organic chemist.

A suitable protecting group $R^4$, as employed in Scheme II, is any one of the many such groups known in the art and includes any appropriate protecting group as defined hereinbefore. Examples of such groups are given in Scheme II. The conditions for the introduction and removal of such protecting groups are described in standard textbooks of organic chemistry such as, for example, "Protective Groups in Organic Synthesis" by T. W. Green (J. Wiley and Sons, 1981).

(c) The alkylation, in the presence of a suitable base as defined hereinbefore, of a compound of the formula IV with a compound of the formula $R^1$—Z, wherein $R^1$ and Z have the meanings defined hereinbefore, provided that, when there is an amino, imino, alkylamino or hydroxy group in $Ar^1$, $Ar^2$, $R^2$ or $R^3$ any amino, imino, alkylamino or hydroxy group may be protected by a conventional protecting group or alternatively any such group need not be protected; whereafter any undesired protecting group in $Ar^1$, $Ar^2$, $R^2$ or $R^3$ is removed by conventional means.

The tertiary alcohol starting material of the formula IV may be obtained by standard procedures of organic chemistry. The preparation of examples of such tertiary alcohols is described within the accompanying non-limiting Examples which are provided for the purpose of illustration only. Further required tertiary alcohol starting materials are obtainable by analogous procedures to those described or by modification thereto which are within the ordinary skill of an organic chemist. Conveniently, and as illustrated in accompanying Scheme III (set out hereinafter), intermediates of the formulae $Ar^1$—$X^1$—$Ar^2$—Y, wherein $Ar^1$, $X^1$ and $Ar^2$ have the meanings defined hereinbefore and Y is, for example, a halogeno, formyl, alkanoyl, nitrile or alkoxycarbonyl group may be utilised in the preparation of the tertiary alcohol starting material of the formula IV.

(d) For the production of those compounds of the formula I wherein $Ar^1$ or $Ar^2$ bears a sulphinyl or sulphonyl group; wherein $X^1$ is a sulphinyl or sulphonyl group; or wherein $R^2$ and $R^3$ together form a group of the formula —$A^2$—$X^2$—$A^3$— and $X^2$ is a sulphinyl or sulphonyl group, and which may bear one or two alkylsulphinyl or alkylsulphonyl groups; the oxidation of a compound of the formula I wherein $Ar^1$ or $Ar^2$ bears a thio group; wherein $X^1$ is a thio group; or wherein $R^2$ and $R^3$ together form a group of the formula —$A^2$—$X^2$—$A^3$— and $X^2$ is a thio group, and which may bear one or two alkylthio groups.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(e) For the production of those compounds of the formula I wherein $Ar^1$ or $Ar^2$ bears an alkanoylamino substituent, the acylation of a compound of the formula I wherein $Ar^1$ or $Ar^2$ bears an amino substituent.

A suitable acylating agent is, for example, any agent known in the art for the acylation of amino to acylamino, for example an acyl halide, for example a (2-6-C)alkanoyl chloride or bromide, in the presence of a suitable base, an alkanoic acid anhydride, for example a (2-6C)alkanoic acid anhydride, or an alkanoic acid mixed anhydride, for example the mixed anhydride formed by the reaction of an alkanoic acid and a (1-4C-)alkoxycarbonyl halide, for example a (1-4C)alkoxycarbonyl chloride, in the presence of a suitable base. In general the reaction is carried out in a suitable solvent or diluent such as methylene chloride, acetone, tetrahydrofuran or tert-butyl methyl ether and at a temperature, for example, at or near ambient temperature, that is in the range 15° to 35° C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate.

(f) For the production of those compounds of the formula I wherein $R^1$ is alkanoyl or benzoyl optionally bearing a substituent as defined hereinbefore, the acylation of a compound of the formula I wherein $R^1$ is hydrogen. For the production of those compounds of the formula I wherein $R^1$ is alkanoyl the acylation reaction may be carried out using, for example, a suitable acylating agent as defined hereinbefore. For the production of those compounds of the formula I wherein $R^1$ is benzoyl optionally bearing a substituent the acylation may be carried out using, for example, a benzoyl halide, for example a benzoyl chloride or bromide, in the presence of a suitable base as defined hereinbefore.

(g) For the production of those compounds of the formula I wherein $Ar^1$ or $Ar^2$ bears an alkyl or substituted alkyl substituent on an available nitrogen atom, or wherein $Ar^1$ or $Ar^2$ bears an alkoxy or substituted alkoxy substituent, the alkylation of a compound of the formula I wherein $Ar^1$ or $Ar^2$ bears a hydrogen atom on said available nitrogen atom, or wherein $Ar^1$ or $Ar^2$ bears a hydroxy substituent.

A suitable alkylating agent is, for example, any agent known in the art for the alkylation of an available nitrogen atom, or of hydroxy to alkoxy or substituted alkoxy, for example an alkyl or substituted alkyl halide, for example a (1-6C)alkyl chloride, bromide or iodide or a substituted (1-4C)alkyl chloride, bromide or iodide, in the presence of a suitable base. A suitable base for the alkylation reaction is, for example, an alkali or alkaline earth metal carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, dimethylsulphoxide, acetone, 1,2-dimethoxyethane or tetrahydrofuran, and at a temperature in the range, for example, 10° to 150° C., conveniently at or near ambient temperature.

(h) For the production of those compounds of the formula I wherein $Ar^1$ or $Ar^2$ bears an amino substituent, the reduction of a compound of the formula I wherein $Ar^1$ or $Ar^2$ bears a nitro substituent.

A suitable reducing agent is, for example, any agent known in the art for the reduction of a nitro group to an amino group. Thus, for example, the reduction may be carried out by the hydrogenation of a solution of the nitro compound in an inert solvent or diluent in the presence of a suitable metal catalyst, for example finely divided platinum metal (obtained by the reduction of platinum oxide in situ). A suitable inert solvent or diluent is, for example, an alcohol, for example methanol, ethanol or isopropanol, or an ether, for example tetrahydrofuran.

A further suitable reducing agent is, for example, an activated metal such as activated iron (produced by washing iron powder with a dilute solution of an acid such as hydrochloric acid). Thus, for example, the reduction may be carried out by heating a mixture of the nitro compound and the activated metal in a suitable solvent or diluent such as a mixture of water and an alcohol, for example, methanol or ethanol, to a temperature in the range, for example 50° to 150° C., conveniently at or near 70° C.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formulae III and IV and these are provided as a further feature of the invention.

As stated previously, the diaryl ether heterocycles of the formula I are inhibitors of the enzyme 5-LO. The effects of this inhibition may be demonstrated using one or more of the standard procedures set out below:

a) An in vitro spectrophotometric enzyme assay system, which assesses the inhibitory properties of a test compound in a cell free system using 5-LO isolated from guinea pig neutrophils and as described by D. Aharony and R. L. Stein (*J. Biol. Chem.*, 1986, 261(25), 11512–11519). This test provides a measure of the intrinsic inhibitory properties against soluble 5-LO in an extracellular environment.

b) An in vitro assay system involving incubating a test compound with heparinised human blood, prior to challenge with the calcium ionophore A23187 and then indirectly measuring the inhibitory effects on 5-LO by assaying the amount of $LTB_4$ using the specific radioimmunoassay described by Carey and Forder (F. Carey and R. A. Forder, *Brit. J. Pharmacol.* 1985, 84, 34P) which involves the use of a protein-$LTB_4$ conjugate produced using the procedure of Young et alia (*Prostaglandins*, 1983, 26(4), 605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TxB_2)$ described by Carey and Forder (see above). This test $B_2(TxB_2)$ described by Carey and Forder (see above). This test provides an indication of the effects of a test compound against 5-LO and also cylooxygenase in the presence of blood cells and proteins. It permits the selectivity of the inhibitory effect on 5-LO or cyclooxygenase to be assessed.

c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

d) An in vitro assay system involving the measurement of the inhibitory properties of a test compound against the liberation of $LTC_4$ and $PGE_2$ induced by zymosan on mouse resident peritoneal macrophages, using the procedure of Humes (J. L. Humes et alia, *Biochem. Pharmacol.*, 1983, 32, 2319–2322) and conventional radioimmunoassay systems to measure $LTC_4$ and $PGE_2$. This test provides an indication of inhibitory effects against 5-LO and cyclooxygenase in a non-proteinaceous system.

e) An in vivo system involving the measurement of the effects of a test compound in inhibiting the inflammatory response to arachidonic acid in the rabbit skin model developed by D. Aked et alia (*Brit. J. Pharmacol.*, 1986, 89, 431–438). This test provides an in vivo model for 5-LO inhibitors administered topically or orally.

f) An in vivo system involving measuring the effects of a test compound administered orally or intravenously on a leukotriene dependent bronchoconstriction induced by an antigen challenge in guinea pigs pre-dosed with an antihistamine (mepyramine), a $\beta$-adrenergic blocking agent (propranolol) and a cyclooxygenase inhibitor (indomethacin), using the procedure of W. H. Anderson et alia (*British J Pharmacology*, 1983, 78(1), 67–574). This test provides a further in vivo test for detecting 5-LO inhibitors.

g) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days). At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in one or more of the above tests a)–f):

Test a): $IC_{50}$ in the range, for example, 0.01–30 $\mu M$;
Test b): $IC_{50}$ ($LTB_4$) in the range, for example, 0.01–40 $\mu M$; $IC_{50}$ ($TxB_2$) in the range, for example, 40–200 $\mu M$;

Test c): oral $ED_{50}(LTB_4)$ in the range, for example, 1–100 mg/kg;
Test d): $IC_{50}$ ($LTC_4$) in the range, for example, 0.001–1 $\mu M$; $IC_{50}$ ($PGE_2$) in the range, for example, 20–1000 $\mu M$;
Test e): inhibition of inflammation in the range, for example, 0.3–100 $\mu g$ intradermally;
Test f): $ED_{50}$ in the range, for example, 0.5–10 mg/kg i.v.;
Test g): oral $ED_{50}(LTB_4)$ in the range, for example, 0.5–50 mg/kg.

No overt toxicity or other untoward effects are present in tests c), e), f) and/or g) when compounds of the formula I are administered at several multiples of their minimum inhibitory dose or concentration.

Thus, by way of example, the compound 4-methoxy-4-[3-(naphth-2-ylthio)phenyl]tetrahydropyran has an $IC_{50}$ of <0.15 $\mu M$ against $LTB_4$ in test b), an oral $ED_{50}$ of 3 mg/kg versus $LTB_4$ in test c) and an oral $ED_{50}$ of <10 mg/kg versus $LTB_4$ in test g); and the compound (2S,4R)-4-[5-fluoro-3-(4-tert-butylphenylthio)phenyl]-4-methoxy-2-methyltetrahydropyran has an $IC_{50}$ of <0.15 $\mu M$ against $LTB_4$ in test b), an oral $ED_{50}$ of 2 mg/kg versus $LTB_4$ in test c) and an oral $ED_{50}$ of 0.75 mg/kg versus $LTB_4$ in test g). In general those compounds of the formula I which are particularly preferred have an $IC_{50}$ of <1 $\mu M$ against $LTB_4$ in test b), and an oral $ED_{50}$ of <100 mg/kg against $LTB_4$ in test c).

These compounds are examples of diaryl ether heterocycles of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a diaryl ether heterocycle of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients.

The amount of active ingredient (that is a diaryl ether heterocycle of the formula I or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a heterocycle of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a diaryl ether heterocycle of the formula I will naturally vary according to the nature and severity of the conditions, the age and sex of the animal or patient and the route of administration, according to well known principles of medicine. As mentioned above, diaryl ether heterocycles of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a diaryl ether heterocycle of the formula I, or a pharmaceutically-acceptable salt thereof as defined hereinbefore, in conjunction or admixture with a cyclooxygenase inhibitory non-steroidal anti-inflammatory agent (such as mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The compounds of the formula I may also be used in combination with leukotriene antagonists such as those disclosed in European Patent Specification Nos. 179619, 199543 and 220066, which are incorporated herein by way of reference.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18°-25° and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture;

(viii) the specific rotation, [alpha]$^t$, of plane polarised light was determined using the sodium D line (5890 Ansgstroms), at 20° C., and generally using sample concentrations of approximately 1 g/100 ml; and (ix) the following abbreviations have been used:

| THF | tetrahydrofuran; |
|---|---|
| DMSO | dimethylsulphoxide; |
| DMF | N,N-dimethylformamide; |

EXAMPLE 1

A solution of 4-(3-bromophenyl)-4-methoxytetrahydropyran (3 g) in butanol (1 ml) was added to sodium butoxide [prepared by the addition of butanol (12 ml) to sodium hydride (60% w/w dispersion in mineral oil; 1.43 g)] and the mixture was stirred at ambient temperature for 10 minutes. 2-Naphthalenethiol (1.83 g), tetrakis(triphenylphosphine)palladium (0.51 g) and DMSO (12 ml) were added and the mixture was heated to 100° C. for 36 hours. The mixture was cooled to ambient temperature and partitioned between diethyl ether and brine. The organic phase was dried (MgSO4) and evaporated. The residue was purified by column chromatography using increasingly polar mixtures of hexane and ethyl acetate as eluent. There was thus obtained 4-methoxy-4-[3-(naphth-2-ylthio)phenyl]tetrahydropyran (0.42 g, 11%), m.p. 66°–67° C.

The 4-(3-bromophenyl)-4-methoxytetrahydropyran used as a starting material was obtained as follows:

A solution of 1,3-dibromobenzene (23.8 g) in THF (120 ml) was cooled to −78° C. and n-butyl-lithium (1.6 M in hexane, 62.5 ml) was added dropwise. The mixture was stirred at −78° C. for 30 minutes and a solution of tetrahydropyran-4-one (10 g) in THF (40 ml) was added. The resultant suspension was stirred at −78° C. for 1 hour, allowed to warm to ambient temperature and then stirred for 30 minutes. The mixture was poured into brine (250 ml) and extracted with diethyl ether. The organic phase was dried (MgSO4) and evaporated. The residue was triturated under hexane and the resultant solid (16.8 g) was filtered off.

A solution of the product so obtained in DMF (100 ml) was added dropwise to a slurry of sodium hydride (60% w/w dispersion in mineral oil; 5.25 g) in DMF (10 ml) and the mixture was stirred at ambient temperature for 90 minutes. Methyl iodide (36.5 g) was added and the mixture was stirred at ambient temperature for 16 hours. Ethanol (2 ml) and water (500 ml) was added in turn and the mixture was extracted with diethyl ether (3×200 ml). The combined extracts were washed with water, dried (MgSO4) and evaporated. The residue was purified by column chromatography using increasingly polar mixtures of hexane and ethyl acetate as eluent. There was thus obtained the required starting material (12 g, 44%) as a gum.

NMR Spectrum (CDCl3, δ values) 1.88–2.1 (m, 4H), 3.0 (s, 3H), 3.78–3.95 (m, 4H), 7.2–7.35 (m, 2H), 7.42 (m, 1H), 7.55 (m, 1H).

EXAMPLE 2

Using a similar procedure to that described in Example 1, except that the appropriate thiol was used in place of 2-naphthalene thiol and that the products were purified by column chromatography on reversed-phase silica using decreasingly polar mixtures of methanol and water as eluent, there were obtained the compounds described in the following table:

TABLE I

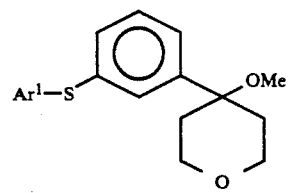

| Ex. 2 Compd. No. | Ar¹ | m.p. (°C.) | Yield (%) |
|---|---|---|---|
| 1[a] | phenyl | oil | 55 |
| 2[b] | 3,4-dichlorophenyl | oil | 32 |
| 3[c] | 4-tert-butylphenyl | oil | 56 |

Notes
[a]The product gave the following NMR data: (CDCl3, δ values) 1.9–2.1(m, 4H), 2.97(s, 3H), 3.75–3.9(m, 4H), 7.2–7.4(m, 9H).
[b]The product gave the following NMR data: (CDCl3, δ values) 1.9–2.05(m, 4H), 2.97(s, 3H), 3.77–3.9(m, 4H), 7.1(doublet of doublets, 2H), 7.13–7.4(m, 5H), 7.45(m, 1H).
[c]The product gave the following NMR data: (CDCl3, δ values) 1.31(s, 9H), 1.85–2.1(m, 4H), 2.95(s, 3H), 3.75–3.92(m, 4H), 7.15–7.4(m, 8H).

EXAMPLE 3

A solution of 4-hydroxy-4-[3-(naphth-2-ylsulphonyl)phenyl]tetrahydropyran (0.56 g) in THF (5 ml) was added dropwise to a slurry of sodium hydride (60% w/w dispersion in mineral oil; 0.26 g) and the mixture was stirred at ambient temperature for 30 minutes. Methyl iodide (0.91 g) was added and the mixture was stirred at ambient temperature for 90 minutes. Methanol (2 drops) and water (50 ml) were added in turn and the mixture was extracted with diethyl ether (4×15 ml). The combined organic extracts were dried (MgSO4) and evaporated. The residue was recrystallised from a mixture of hexane and ethyl acetate. The mother liquors were evaporated and the resultant residue was purified by column chromatography using increasingly polar mixtures of hexane and ethyl acetate as eluent. There was thus obtained, by combining the two batches of product, 4-methoxy-4-[3-(naphth-2-ylsulphonyl)phenyl]tetrahydropyran (0.37 g, 22%), m.p. 132°–134° C.

The 4-hydroxy-4-[3-(naphth-2-ylsulphonyl)phenyl]tetrahydropyran used as a starting material was obtained as follows:

A mixture of 2-naphthalenethiol (3.2 g), 3-iodobromobenzene (6.7 g), potassium carbonate (1.4 g), cuprous chloride (0.4 g) and DMF (4 ml) was heated to reflux for 1 hour. The mixture was allowed to cool to ambient temperature and was partitioned between diethyl ether and water. The mixture was filtered and the organic layer was separated, dried (MgSO4) and evaporated. The residue was taken up in ethyl acetate, decolourised by treatment with charcoal, reisolated and purified by recrystallisation from methanol to give 3-bromophenyl 2-naphthyl sulphide (3.9 g, 65%), m.p. 68°–70° C.

A solution of potassium peroxymonosulphate (17.7 g) in water (30 ml) was added to a mixture of the product so obtained (3.0 g) and ethanol (30 ml) which had been cooled to 0° C. in an ice-bath. The mixture was stirred at ambient temperature for 18 hours and at 60° C. for 5 hours. The mixture was cooled to ambient temperature and partitioned between chloroform and water. The organic phase was dried (MgSO4) and evaporated to give 3-bromophenyl 2-naphthyl sulphone (3 g) as a solid which was used without further purification.

A solution of a portion (1.5 g) of the product so obtained in THF (10 ml) was cooled to −78° C. and n-butyl-lithium (1.6M in hexane; 2.7 ml) was added dropwise. The mixture was stirred at −78° C. for 30 minutes and a solution of tetrahydropyran-4-one (0.43 g) in THF (5 ml) was added. The mixture was stirred at −78° C. for 1 hour, allowed to warm to ambient temperature and then stirred for 15 minutes. Brine (50 ml) was added and the mixture was extracted with diethyl ether (3×50 ml). The combined extracts were dried (MgSO$_4$) and evaporated. The residue was purified by column chromatography using increasingly polar mixtures of hexane and ethyl acetate as eluent. There was thus obtained the required starting material as a viscous oil which slowly crystallised on standing (0.56 g, 35%).

EXAMPLE 4

Using a similar procedure to that described in Example 3, except that the appropriate 4-hydroxytetrahydropyran was used in place of 4-hydroxy-4-[3-(naphth-2-ylsulphonyl)phenyl]tetrahydropyran, there were obtained the compounds described in the following table:

TABLE II

Ar$^1$—X$^1$—[phenyl ring with R substituent]—[tetrahydropyran with MeO]

| Ex. 4 Compd. No. | Ar$^1$ | X$^1$ | R | m.p. (°C.) | Yield (%) |
|---|---|---|---|---|---|
| 1$^a$ | 2-naphthyl | S | CF$_3$ | oil | 79 |
| 2$^b$ | 4-(2-cyanoprop-2-yl)phenyl | S | CF$_3$ | oil | 97 |

Notes a. The product gave the following NMR data: (CDCl$_3$, δ values) 1.9 (m, 4H), 2.95 (s, 3H), 3.8 (m, 4H), 7.4–7.55 (m, 6H), 7.75–7.84 (m, 3H), 7.95 (d, 1H).

The 4-hydroxy-4-[3-(naphth-2-ylthio)-5-trifluoromethylphenyl]tetrahydropyran used as a starting material was obtained as follows:

Sodium hydride (60% w/w dispersion in mineral oil; 0.5 g) was added portionwise to a mixture of 2-naphthalenethiol (1.42 g) and DMA (30 ml) and the mixture was stirred at ambient temperature for 1 hour. A solution of 1-bromo-3-fluoro-5-trifluoromethylbenzene (2.43 g) in DMA (10 ml) was added and the mixture was stirred at ambient temperature for 16 hours. The mixture was partitioned between ethyl acetate and water. The organic layer was washed with brine (50 ml), dried (MgSO$_4$) and evaporated. The residue was purified by column chromatography using hexane as eluent. There was thus obtained 3-bromo-5-trifluoromethylphenyl 2-naphthyl sulphide (1.37 g, 40%), as an oil.

A solution of the product so obtained in THF (10 ml) was cooled to −60° C. and n-butyl-lithium (1.6M in hexane; 2.3 ml) was added dropwise. The mixture was stirred at −60° C. for 30 minutes and a solution of tetrahydropyran-4-one (0.35 ml) was added. The mixture was allowed to warm to ambient temperature. A saturated aqueous ammonium chloride solution was added and the mixture was extracted with ethyl acetate (3×25 ml). The combined extracts were washed with water and with brine, dried (MgSO$_4$) and evaporated. The residue was purified by column chromatography using increasingly polar mixtures of methylene chloride and ethyl acetate as eluent. There was thus obtained the required starting material (0.63 g, 43%) as an oil which was used without further purification.

b. The product gave the following NMR data: (CDCl$_3$, δ values) 1.75 (s, 6H), 1.85–2.05 (m, 4H), 2.96 (s, 3H), 3.8 (m, 4H), 7.37–7.55 (m, 7H, aromatic).

The 4-[3-(4-(2-cyanoprop-2-yl)phenylthio)-5-trifluoromethylphenyl]-4-hydroxytetrahydropyran used as a starting material was obtained as follows:

Using a similar procedure to that described in the 1st paragraph of Note a. above 4-toluenethiol was reacted with 1-bromo-3-fluoro-5-trifluoromethylbenzene to give 3-bromo-5-trifluoromethylphenyl 4-tolyl sulphide in 63% yield as an oil.

A mixture of the product so obtained (7.5 g), N-bromosuccinimide (4.25 g), benzoyl peroxide (0.2 g) and carbon tetrachloride (40 ml) was heated to reflux for 4 hours. The mixture was cooled to ambient temperature and filtered. The filtrate was evaporated and the residue was purified by column chromatography using a 10:1 v/v mixture of hexane and ethyl acetate as eluent to give 3-bromo-5-trifluoromethylphenyl 4-bromomethylphenyl sulphide (7.3 g, 79%), as an oil.

A mixture of a portion (7.0 g) the product so obtained, potassium cyanide (4 g), tetrabutylammonium bromide (0.32 g), methylene chloride (20 ml) and water (20 ml) was stirred and heated to reflux for 3 hours. The mixture was cooled to ambient temperature and the organic phase was separated, washed with water and with brine, dried (MgSO$_4$) and evaporated. The residue was purified by column chromatography using hexane as eluent to give 3-bromo-5-trifluoromethylphenyl 4-cyanomethylphenyl sulphide (3.8 g, 62%) as an oil.

A mixture of the product so obtained, methyl iodide (3.1 ml) and DMF (20 ml) was added to a suspension of sodium hydride (60% w/w dispersion in mineral oil; 0.8 g) in DMF (10 ml) which was cooled to 5° C. The mixture was stirred at 5° C. for 15 minutes and then allowed to warm to ambient temperature. The mixture was poured into a mixture of ice and water and extracted with ethyl acetate (3×50 ml). The combined extracts were washed with water and brine, dried (MgSO$_4$) and evaporated. The residue was purified by column chromatography using methylene chloride as eluent to give 3-bromo-5-trifluoromethylphenyl 4-(2-cyanoprop-2-yl)phenyl sulphide (2.4 g, 59%), as an oil.

Using a similar procedure to that described in Note a. immediately above a portion (1 g) of the product so obtained was lithiated and the organo-lithium reagent so formed was reacted with tetrahydropyran-4-one. There was thus obtained the required starting material as an oil in 24% yield.

NMR Spectrum 1.5–1.7 (m, 2H), 1.75 (s, 6H), 2.0–2.2 (m, 2H), 3.85–3.95 (d, 4H), 7.35–7.5 (m, 5H), 7.65 (d, 2H).

EXAMPLE 5

Using the conditions described in Example 3 above (2RS,4SR)-4-[3-(4-(2-cyanoprop-2-yl)phenylthio-5-trifluoromethylphenyl]-4-hydroxy-2-methyltetrahydropyran (0.084 g) was reacted with methyl iodide to give (2RS,4SR)-4-[3-(4-(2-cyanoprop-2-yl)phenylthio)-5-trifluoromethylphenyl]-4-methoxy-2-methyltetrahydropyran (0.052 g, 60%) as an oil.

NMR Spectrum (CDCl3, δ values) 1.2 (d, 3h), 1.45-1.55 (t, 1h), 1.75 (s, 6H), 1.85-2.0 (m, 3H), 2.95 (s, 3H), 3.85-3.95 (m, 3H), 7.35-7.57 (m, 7H, aromatic).

The (2RS,4SR)-4-[3-(4-(2-cyanoprop-2-yl)phenylthio)-5-trifluoromethylphenyl]-4-hydroxy-2-methyltetrahydropyran used as a starting material was obtained as follows:

The procedure described in the 5th paragraph of the portion of Note b. within Example 4 which is concerned with the preparation of starting materials was repeated except that 2-methyltetrahydropyran-4-one (*J. Amer. Chem. Soc.*, 1982, 104, 4666) was used in place of tetrahydropyran-4-one. There was thus obtained and separated a mixture of diastereoisomers:

the required starting material as a less polar isomer and as an oil in 14% yield, the (2RS,4SR)-isomer, having the 2-methyl and 4-hydroxy substituents in a trans-relationship; and a more polar isomer as an oil in 27% yield, the (2SR,4SR)-isomer, having the 2-methyl and 4-hydroxy substituents in a cis-relationship.

EXAMPLE 6

The procedure described in Example 5 was repeated except that the (2SR,4SR)-diastereoisomer described in the portion of Example 5 which is concerned with the preparation of starting materials was used as a starting material. There was thus obtained (2SR,4SR)-4-[3-(4-(2-cyanoprop-2-yl)phenylthio)-5-trifluoromethylphenyl]-4-methoxy-2-methyltetrahydropyran (0.03 g, 18%) as an oil.

NMR Spectrum (CDCl3, δ values) 1.2 (d, 3H), 1.4-1.5 (m, 1H), 1.74 (s, 6H), 1.85-2.05 (m, 1H), 2.2-2.3 (m, 2H), 2.86 (s, 3H), 3.2-3.35 (m, 2H), 3.9-4.0 (m, 1H), 7.37-7.52 (m, 7H, aromatic).

EXAMPLE 7

Sodium metaperiodate (0.07 g) was added to a mixture of 4-methoxy-4-[3-(naphth-2-ylthio)-5-trifluoromethylphenyl]tetrahydropyran (0.22 g; Example 4, Compound No. 1), THF (1 ml), methanol (1 ml) and water (1 ml) which had been cooled to 0° C. The mixture was allowed to warm to ambient temperature and was stirred for 16 hours. A second portion of sodium metaperiodate was added and the mixture was stirred for 48 hours. The mixture was evaporated and the residue was partitioned between ethyl acetate and water. The organic phase was washed with water and with brine, dried (MgSO4) and evaporated. The residue was purified by column chromatography using increasingly polar mixtures of methylene chloride and ethyl acetate as eluent. There was thus obtained 4-methoxy-4-[3-(naphth-2-ylsulphinyl)-5-trifluoromethylphenyl]tetrahydropyran (0.03 g, 13%) as an oil.

NMR Spectrum (CDCl3, δ values) 1.8-2.1 (m, 4H), 2.9 (s, 3H), 3.75-3.9 (m, 4H), 7.5-7.65 (m, 3H), 7.7 (s, 1H), 7.8-8.0 (m, 5H), 8.3 (s, 1H).

EXAMPLE 8

Using a similar procedure to that described in Example 3, except that the appropriate 4-hydroxytetrahydropyran was used in place of 4-hydroxy-4-[3-(naphth-2-ylsulphonyl)phenyl]tetrahydropyran, there were obtained the compounds described in the following table:

TABLE III

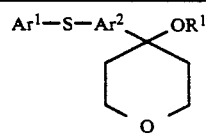

| Ex. 8 Compd. No. | Ar¹ | Ar² | R¹ | m.p. (°C.) | Yield (%) |
|---|---|---|---|---|---|
| 1[a] | 2-naphthyl | 1,3-phenylene | allyl* | oil | 80 |
| 2[b] | 2-naphthyl | 5-fluoro-1,3-phenylene | Me | oil | 64 |
| 3[c] | 2-naphthyl | 5-fluoro-1,3-phenylene | allyl* | oil | 46 |
| 4[d] | 2-naphthyl | 5-fluoro-1,3-phenylene | 2-propynyl+ | oil | 33 |
| 5[e] | 2-naphthyl | 2,5-difluoro-1,3-phenylene | Me | 116–118 | 53 |
| 6[f] | 2-naphthyl | 2,5-difluoro-1,3-phenylene | allyl* | oil | 47 |
| 7[g] | 4-tert-butyl-phenyl | 5-fluoro-1,3-phenylene | Me | 75–76 | 76 |
| 8[h] | 4-tert-butyl-phenyl | 5-fluoro-1,3-phenylene | allyl* | oil | 65 |
| 9[i] | 4-tert-butyl-phenyl | 2,5-difluoro-1,3-phenylene | Me | 98–99 | 70 |
| 10[j] | 4-(2-cyanoprop-2-yl)phenyl | 5-fluoro-1,3-phenylene | allyl* | oil | 66 |
| 11[k] | 4-(2-cyanoprop-2-yl)phenyl | 5-fluoro-1,3-phenylene | Me | 67–68 | 62 |
| 12[k] | 3-(2-cyanoprop-2-yl)phenyl | 5-trifluoromethyl-1,3-phenylene | Me | oil | 64 |
| 13[l] | 4-(1-cyano-cyclopent-1-yl)-phenyl | 5-trifluoromethyl-1,3-phenylene | Me | oil | 88 |
| 14[m] | 4-tert-butyl- | 5-bromo-1,3- | Me | oil | 45 |

TABLE III-continued

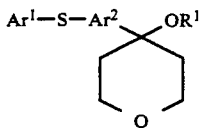

Ex. 8

| Compd. No. | Ar¹ | Ar² | R¹ | m.p. (°C.) | Yield (%) |
|---|---|---|---|---|---|
| | phenyl | phenylene | | | |

NOTES

* Allyl bromide was used in place of methyl iodide as the alkylating agent.

+ 2-Propynyl bromide was used in place of methyl iodide as the alkylating agent.

a. The product gave the following NMR data: (CDCl$_3$, δ values) 2.0 (m, 4H), 3.55 (m, 2H), 3.7–4.0 (m, 4H), 5.0–5.3 (m, 2H), 5.7 (m, 1H), 7.2–7.5 (m, 7H), 7.7–7.9 (m, 4H).

The 4-hydroxy-4-[3-(naphth-2-ylthio)phenyl]tetrahydropyran used as a starting material was obtained from 2-naphthalenethiol using the procedures described in the portion of Example 3 which is concerned with the preparation of starting materials except that the oxidation step utilizing potassium peroxymonosulphate was not carried out. There was thus obtained the required starting material in 45% yield as an oil.

NMR Spectrum (CDCl$_3$, δ values) 1.6 (m, 3H), 2.1 (m, 2H), 3.8 (m, 4H), 7.2–7.6 (m, 7H), 7.7–7.9 (m, 4H).

b. After the methyl iodide had been added, 1,4,7,10,13-pentaoxacyclopentadecane (hereinafter 15-crown-5, 10 mg) was added and the reaction mixture was stirred at ambient temperature for 2 days.

The product gave the following NMR data: (CDCl$_3$, δ values) 1.75–2.0 (m, 4H), 2.97 (s, 3H), 3.6–4.0 (m, 4H), 6.75–7.25 (m, 3H), 7.3–7.6 (m, 3H), 7.6–8.0 (m, 4H).

The 4-[5-fluoro-3-(naphth-2-ylthio)phenyl]-4-hydroxytetrahydropyran used as a starting material was obtained as follows:

Sodium hydride (50% w/w dispersion in mineral oil, 0.58 g) was added portionwise to a mixture of 2-naphthalenethiol (1.6 g) and DMA (15 ml) and the mixture was stirred at ambient temperature for 1.5 hours. 1-Bromo-3,5-difluorobenzene (1.93 g) was added and the mixture was heated to 60° C. for 3 hours. The mixture was allowed to cool to ambient temperature and partitioned between diethyl ether and water. The organic phase was washed with brine (50 ml), dried (MgSO$_4$) and evaporated. The residue was purified by column chromatography using petroleum ether (b.p. 40°–60° C.) as eluent. There was thus obtained 3-bromo-5-fluorophenyl 2-naphthyl sulphide (2.1 g, 63%) as an oil.

After repetition of the above reaction a solution of a portion (2.5 g) of the product so obtained in THF (50 ml) was cooled to −78° C. and n-butyl-lithium (1.6M in hexane, 5.63 ml) was added dropwise. The mixture was stirred at −78° C. for 10 minutes and a solution of tetrahydropyran-4-one (0.76 ml) in THF (10 ml) was added. The mixture was stirred and allowed to warm to ambient temperature. Water (10 ml) was added and then the reaction mixture was acidified by the addition of 2N hydrochloric acid solution. The mixture was extracted with diethyl ether (3×50 ml). The combined extracts were washed with brine (50 ml), dried (MgSO$_4$) and evaporated. The residue was triturated under petroleum ether (b.p. 60°–80° C.). There was thus obtained the required starting material (1.62 g, 61%), m.p. 100° C.

c. DMF was used in place of THF as the reaction solvent.

The product gave the following NMR data: (CDCl$_3$, δ values) 1.75–2.0 (m, 4H), 3.5–4.0 (m, 6H), 4.9–5.4 (m, 2H), 5.5–6.0 (m, 1H), 6.75–7.25 (m, 3H), 7.3–7.6 (m, 3H), 7.6–8.0 (m, 4H).

d. DMF was used in place of THF as the reaction solvent.

The product gave the following NMR data: (CDCl$_3$, δ values) 1.75–2.1 (m, 4H), 2.31 (t, 1H), 3.6–4.0 (m, 6H), 6.75–7.25 (m, 3H), 7.3–7.6 (m, 3H), 7.65–8.0 (m, 4H).

e. The 4-[2,5-difluoro-3-(naphth-2-ylthio)phenyl]-4-hydroxytetrahydropyran used as a starting material was obtained as follows:

Sodium hydride (50% w/w dispersion in mineral oil, 0.6 g) was added portionwise to a mixture of 2-naphthalenethiol (1.9 g) and DMA (40 ml) and the mixture was stirred at ambient temperature for 1 hour. 1-Bromo-2,3,5-trifluorobenzene (2.25 g) was added and the mixture was stirred at ambient temperature for 16 hours. The mixture was partitioned between ethyl acetate and water. The organic phase was washed with brine (50 ml), dried (MgSO$_4$) and evaporated. The residue was purified by column chromatography using hexane as eluent. There was thus obtained 3-bromo-2,5-difluorophenyl 2-naphthyl sulphide (1.5 g, 40%), as an oil.

A solution of a portion (0.8 g) of the product so obtained in THF (20 ml) was cooled to −70° C. and n-butyl-lithium (1.6M in hexane, 1.3 ml) was added dropwise. The mixture was stirred at −70° C. for 20 minutes and a solution of tetrahydropyran-4-one (0.2 ml) in THF (2 ml) was added dropwise. The mixture was stirred and allowed to warm to −30° C. A saturated aqueous ammonium chloride solution was added and the mixture was allowed to warm to ambient temperature and partitioned between ethyl acetate and water. The organic phase was washed with water (2×50 ml) and with brine, dried (MgSO$_4$) and evaporated. The residue was purified by column chromatography using initially methylene chloride and then a 19:1 v/v mixture of methylene chloride and ethyl acetate as eluent. There was thus obtained the required starting material (0.53 g, 62%), mp. 122°–125° C.

f. The product gave the following NMR data: (CDCl$_3$, δ values) 2.04–2.21 (m, 4H), 3.69–3.74 (q, 2H), 3.85–3.96 (m, 4H), 5.10–5.16 (d, 1H), 5.25–5.34 (d, 1H), 5.79–5.96 (m, 1H), 6.60–6.68 (m, 1H), 7.4–7.9 (m, 7H), 7.99 (s, 1H).

g. The 4-[5-fluoro-3-(4-tert-butylphenylthio)phenyl]-4-hydroxytetrahydropyran used as a starting material was obtained using the procedures described in the portion of Note b. above which is concerned with the preparation of starting materials except that 4-tert-butylphenylthiol was used in place of 2-naphthalenethiol. There was thus obtained the required starting material in 28% yield, m.p. 110° C.

h. DMF was used in place of THF as the reaction solvent.

The product gave the following NMR data: (CDCl₃, δ values) 1.33 (s, 9H), 1.75–2.10 (m, 4H), 3.5–4.0 (m, 6H), 5.0–5.4 (m, 2H), 5.6–6.1 (m, 1H), 6.65–7.15 (m, 3H), 7.4 (s, 4H).

i. The 4-[2,5-difluoro-3-(4-tert-butylphenylthio)-phenyl]-4-hydroxytetrahydropyran used as a starting material was obtained using the procedure described in the portion of Note e. above which is concerned with the preparation of starting materials except that 4-tert-butylphenylthiol was used in place of 2-naphthalenethiol. There was thus obtained the required starting material in 12% yield, m.p. 140°–142° C. (recrystallised from hexane).

j. DMF was used in place of THF as the reaction solvent.

The product gave the following NMR data: (CDCl₃, δ values) 1.70 (s, 6H), 1.75–2.1 (m, 4H), 3.5–4.1 (m, 6H), 5.0–5.5 (m, 2H), 5.6–6.1 (m, 1H), 6.75–7.1 (m, 7H).

The 4-[3-(4-(2-cyanoprop-2-yl)phenylthio-5-fluoro-phenyl]-4-hydroxytetrahydropyran used as a starting material was obtained using the procedures described in the portion of Note b. below Table II in example 4 which is concerned with the preparation of starting materials except that 1-bromo-3,5-difluorobenzene was used in place of 1-bromo-3-fluoro-5-trifluoromethylbenzene. There was thus obtained the required starting material in 17% yield, as an oil.

NMR Spectrum (CDCl₃, δ values) 1.75 (s, 6H), 1.5–2.3 (m, 4H), 3.7–3.9 (m, 4H), 6.85 (m, 1H), 7.10 (m, 1H), 7.25 (t, 1H), 7.45 (s, 4H).

k. The product gave the following NMR data: (CDCl₃, δ values) 1.70 (s, 6H), 1.92 (m, 4H), 2.97 (s, 3H), 3.79–3.84 (m, 4H), 7.33–7.49 (m, 7H).

The 4-[3-(3-(2-cyanoprop-2-yl)phenylthio)-5-trifluoromethylphenyl]-4-hydroxytetrahydropyran used as a starting material was obtained using the procedures described in the portion of Note b. below Table II in Example 4 which is concerned with the preparation of starting materials except that 3-toluenethiol was used in place of 4-toluenethiol. There was thus obtained the required starting material in 3% yield, as an oil, NMR Spectrum (CDCl₃, δ values) 1.56 (m, 2H), 1.65 (s, 6H), 2.04–2.09 (m, 2H), 3.86–3.92 (m, 4H), 7.32–7.37 (t, 3H), 7.46 (m, 2H), 7.63 (s, 1H), 7.70 (s, 1H).

l. The product gave the following NMR data: (CDCl₃, δ values) 1.85–2.15 (m, 10H), 2.45–2.55 (m, 2H), 2.98 (s, 3H), 3.8–3.85 (m, 4H), 7.35–7.55 (m, 7H).

The 4-[3-(4-(1-cyanocyclopent-1-yl)phenylthio)-5-trifluoromethylphenyl]-4-hydroxytetrahydropyran used as a starting material was obtained using the procedures described in the portion of Note b. below Table II in Example 4 which is concerned with the preparation of starting materials except that in the fourth paragraph thereof 1,4-dibromobutane was used in place of methyl iodide. There was thus obtained 3-bromo-5-trifluoromethylphenyl 4-(1-cyanocyclopent-1-yl)phenyl sulphide which was reacted with tetrahydropyran-4-one using a similar procedure to that described in Note b. below Table II in Example 4. There was thus obtained the required starting material in an overall yield of 8%, m.p. 95°–98° C.

m. The product gave the following NMR data (CDCl₃, δ values) 1.30 (s, 9H), 1.8–2.0 (m, 4H), 2.95 (s, 3H), 3.73–3.88 (m, 4H), 7.2–7.45 (m, 7H).

The 4-[5-bromo-3-(4-tert-butylphenylthio)phenyl]-4-hydroxytetrahydropyran used as a starting material was obtained as follows:

A mixture of 4-tert-butylthiophenol (1.66 g), 1,3,5-tribromobenzene (3.15 g), cuprous chloride (0.15 g), potassium carbonate (0.7 g) and DMF (3 ml) was heated to reflux for 2 hours. The mixture was cooled to ambient temperature and partitioned between diethyl ether and water. The organic phase was washed with water, dried (MgSO₄) and evaporated. The residue was purified by column chromatography using hexane as eluent. There was thus obtained 3,5-dibromophenyl 4-tert-butylphenyl sulphide (1.3 g, 32%).

A solution of portion (1 g) of the material so obtained in THF (10 ml) cooled to −80° C. and n-butyl-lithium (1.6M in hexane, 1.6 ml) was added dropwise. The mixture was stirred at −80° C. for 30 minutes and tetrahydropyran-4-one (0.23 ml) was added dropwise. The mixture was stirred at −80° C. for 30 minutes. Water (10 ml) was added and the mixture was allowed to warm to ambient temperature and extracted with diethyl ether. The organic phase was dried (MgSO₄) and evaporated. The residue was purified by column chromatography using increasingly polar mixtures of hexane and ethyl acetate as eluent. There was thus obtained the required starting material (0.9 g, 86%).

EXAMPLE 9

Using a similar procedure to that described in Example 3, except that the appropriate 4-hydroxytetrahydropyran was used in place of 4-hydroxy-4-[3-(naphth-2-ylsulphonyl)phenyl]tetrahydropyran, there were obtained the compounds described in the following table:

TABLE IV

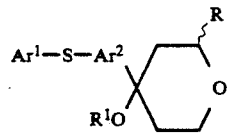

| Ex. 9 Compd. No. | Ar¹ | Ar² | R¹ | R | m.p. (°C.) | Yield (%) |
|---|---|---|---|---|---|---|
| 1[a] | 3-(2-cyanoprop-2-yl)phenyl | 5-trifluoromethyl-1,3-phenylene | Me | alpha-Me | oil | 57 |
| 2[b] | 3-(2-cyanoprop-2-yl)- | 5-trifluoromethyl-1,3- | Me | beta-Me | oil | 66 |

TABLE IV-continued

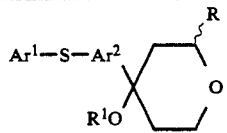

Ex. 9
| Compd. No. | Ar¹ | Ar² | R¹ | R | m.p. (°C.) | Yield (%) |
|---|---|---|---|---|---|---|
| 3[c] | phenyl 4-(3-cyano-pent-3-yl)-phenyl | phenylene 5-trifluoro-methyl-1,3-phenylene | Me | alpha-Me | oil | 83 |
| 4[d] | 4-(3-cyano-pent-3-yl)-phenyl | 5-trifluoro-methyl-1,3-phenylene | Me | beta-Me | oil | 37 |
| 5[e] | 2-naphthyl | 1,3-phenylene | Me | alpha-Me | oil | 80 |
| 6[f] | 2-naphthyl | 1,3-phenylene | Me | beta-Me | oil | 82 |
| 7[g] | 4-tert-butyl-phenyl | 1,3-phenylene | Me | alpha-Me | oil | 65 |
| 8[h] | 4-tert-butyl-phenyl | 1,3-phenylene | Me | beta-Me | oil | 60 |

Notes a. The product gave the following NMR data: (CDCl₃, δ values) 1.2 (d, 3H), 1.5 (s, 2H), 1.7 (s, 6H), 1.9 (m, 2H), 3.0 (s, 3H), 3.9 (t, 3H), 7.31-7.49 (m, 7H).

The (2RS,4SR)-4-[3-(3-(2-cyanoprop-2-yl)phenylthio)-5-trifluoromethylphenyl]-4-hydroxy-2-methyltetrahydropyran used as a starting material was obtained using the procedures described in the portion of Note b. below Table II in Example 4 which is concerned with the preparation of starting materials except that 3-toluenethiol was used in place of 4-toluenethiol and 2-methyltetrahydropyran-4-one was used in place of tetrahydropyran-4-one. There was thus obtained and separated a mixture of diastereoisomers:

the required starting material as a less polar isomer and as an oil in 20% yield, the (2RS,4SR)-isomer, having the 2-methyl and 4-hydroxy substituents in a trans-relationship;

and a more polar isomer as an oil in 26% yield, the (2SR,4SR)-isomer, having the 2-methyl and 4-hydroxy substituents in a cis-relationship.

b. The product gave the following NMR data: (CDCl₃, δ values) 1.2 (d, 3H), 1.5 (m, 1H), 1.74 (s, 6H), 2.0 (m, 1H), 2.25 (m, 2H), 2.9 (s, 3H), 3.27-3.34 (m, 2H), 3.9-4.05 (m, 1H), 7.33-7.53 (m, 7H).

The preparation of (2SR,4SR)-4-[3-(3-(2-cyanoprop-2-yl)phenylthio)-5-trifluoromethylphenyl]-4-hydroxy-2-methyltetrahydropyran, used as a starting material, is described in Note a. immediately above.

c. The product gave the following NMR data: (CDCl₃, δ values) 0.9 (t, 6H), 1.2 (d, 2H), 1.55 (m, 2H), 1.8-2.15 (m, 7H), 2.95 (s, 3H), 3.9 (t, 3H), 7.4 (s, 5H), 7.5 (s, 2H).

The (2RS,4SR)-4-[3-(4-(3-cyanopent-3-yl)phenylthio-5-trifluoromethylphenyl]-4-hydroxy-2-methyltetrahydropyran, used as a starting material, and the corresponding (2SR,4SR)-isomer were obtained using the procedures described in the portion of Note b. below Table II in Example 4 which is concerned with the preparation of starting materials except that ethyl iodide was used in place of methyl iodide and 2-methyltetrahydropyran-4-one was used in place of tetrahydropyran-4-one. There were thus obtained and separated the diastereoisomers: the (2RS,4SR)-isomer as a less polar isomer in 6% yield, NMR Spectrum (CDCl₃, δ values) 0.85-0.95 (t, 6H), 1.2-1.25 (d, 3H), 1.6-1.7 (m, 3H), 1.8-2.1 (m, 5H), 3.85-4.0 (m, 3H), 7.35-7.45 (m, 5H), 7.57-7.65 (d, 2H); and the (2SR,4SR)-isomer as a more polar isomer in 14% yield, NMR Spectrum (CDCl₃, δ values) 0.85-0.95 (t, 6H), 1.2-1.25 (d, 3H), 1.6-1.72 (q, 1H), 1.85-2.15 (m, 5H), 2.2-2.35 (m, 2H), 3.25-3.42 (m, 2H), 3.9-4.05 (m, 1H), 7.35-7.45 (m, 5H), 7.55-7.63 (m, 2H).

d. The product gave the following NMR data: (CDCl₃, δ values) 0.9 (t, 6H), 1.2 (d, 3H), 1.65 (q, 1H), 1.8-2.3 (m, 7H), 2.82 (s, 3H), 3.3 (m, 2H), 3.95 (m, 1H), 7.4-7.5 (m, 7H).

e. DMF was used as the reaction solvent. The product gave the following NMR data (CDCl₃, δ values) 1.18 (d, 3H), 1.5-1.6 (m, 2H), 1.85-2.0 (m, 2H), 2.95 (s, 3H), 3.8-3.95 (m, 3H), 7.2-7.5 (m, 7H), 7.7-7.9 (m, 4H).

The (2RS,4SR)-4-hydroxy-2-methyl-4-[3-(naphth-2-ylthio)phenyl]tetrahydropyran used as a starting material was obtained as follows:

A mixture of magnesium turnings (0.16 g) and THF (5 ml) was heated to reflux and 1,2-dibromoethane (0.03 ml) was added. The mixture was heated to reflux for 15 minutes and a solution of 3-bromophenyl 2-naphthyl sulphide (1.38 g) in THF (2 ml) was added. The mixture was heated to reflux for 1 hour. The mixture was cooled to approximately 0° C. in a bath of a mixture of ice and water and hexane (5 ml) and a solution of 2-methyltetrahydropyran-4-one (0.5 g) in diethyl ether (2 ml) were added in turn. The mixture was stirred at 0° C. for 2 hours and then allowed to warm to ambient temperature. A saturated aqueous ammonium chloride solution (25 ml) was added and the mixture was extracted with diethyl ether (3×30 ml). The combined extracts were dried (MgSO₄) and evaporated. The residue was purified by column chromatography using increasingly polar mixtures of hexane and ethyl acetate as eluent. There were thus separated the following diastereoisomers:

the required starting material as a less polar isomer as an oil (0.24 g, 15%), the (2RS,4SR)-isomer; and a more polar isomer as an oil (0.135 g, 8%), the (2SR,4SR)-isomer.

f. DMF was used as the reaction solvent. The product gave the following NMR data (CDCl₃, δ values) 1.12 (d, 3H), 1.5-1.6 (m, 1H), 1.85-1.98 (m, 1H), 2.25-2.35

(m, 2H), 2.88 (m, 3H), 3.25-3.4 (m, 2H), 3.85-3.98 (m, 1H), 7.2-7.5 (m, 7H), 7.7-7.9 (m, 4H).

g. DMF was used as the reaction solvent. The product gave the following NMR data (CDCl₃, δ values)

1.18 (d, 3H), 1.32 (s, 9H), 1.55 (m, 2H), 1.89-2.3 (m, 2H), 2.95 (s, 3H), 3.82-3.92 (m, 3H), 7.15-7.4 (m, 8H).

The (2RS,4SR)-4-[3-(4-tert-butylphenylthio)phenyl]-4-hydroxy-2-methyltetrahydropyran used as a starting material was obtained in 13% yield by the reaction of the Grignard reagent from 3-bromophenyl 4-tert-butylphenyl sulphide [prepared from 4-tert-butylthiophenol and 3-iodobromobenzene using the procedure described in Note b. below Table III in Example 8] with 2-methyltetrahydropyran-4-one using the procedure described in Note e. immediately above. There was also obtained thereby the corresponding (2SR,4SR)-diastereoisomer in 13% yield.

h. DMF was used as the reaction solvent. The product gave the following NMR data (CDCl₃, δ values) 1.16 (d, 3H), 1.32 (s, 9H), 1.55 (m, 1H), 1.8-2.0 (m, 1H), 2.2-2.38 (m, 2H), 2.86 (s, 3H), 3.2-3.4 (m, 2H), 3.82-3.92 (m, 1H), 7.2-7.4 (m, 8H).

EXAMPLE 10

Using a similar procedure to that described in Example 3, except that the appropriate 4-hydroxytetrahydropyran was used in place of 4-hydroxy-4-[3-(naphth-2-ylsulphonyl)phenyl]tetrahydropyran, unless otherwise stated below, 15-crown-5 (10 mg) was added to the reaction mixture after the alkylating agent had been added, and that the reaction mixture was stirred at ambient temperature for 2 days, there were obtained the compounds described in the following table:

TABLE V

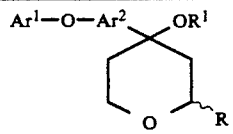

| Ex. 10. Compd. No. | Ar¹ | Ar² | R¹ | R | m.p. (°C.) | Yield (%) |
|---|---|---|---|---|---|---|
| 1ᵃ | 2-naphthyl | 5-fluoro-1,3-phenylene | Me | H | oil | 82 |
| 2ᵇ | 2-naphthyl | 5-fluoro-1,3-phenylene | allyl* | H | oil | 78 |
| 3ᶜ | 2-naphthyl | 5-fluoro-1,3-phenylene | Me | alpha-Me | oil | 87 |
| 4ᵈ | 2-naphthyl | 5-fluoro-1,3-phenylene | Et | alpha-Me | oil | 74 |
| 5ᵉ | 2-naphthyl | 5-fluoro-1,3-phenylene | allyl* | alpha-Me | oil | 60 |
| 6ᶠ | 2-naphthyl | 5-fluoro-1,3-phenylene | allyl* | beta-Me | oil | 89 |
| 7ᵍ | 2-naphthyl | 5-trifluoromethyl-1,3-phenylene | Me | H | 80 | 94 |
| 8ʰ | 2-naphthyl | 5-trifluoromethyl-1,3-phenylene | allyl* | H | 73-74 | 82 |
| 9ⁱ | 2-naphthyl | 5-trifluoromethyl-1,3-phenylene | Me | alpha-Me | oil | 71 |
| 10ʲ | 2-naphthyl | 5-trifluoromethyl-1,3-phenylene | Me | beta-Me | oil | 80 |
| 11ᵏ | 4-tert-butylphenyl | 5-fluoro-1,3-phenylene | Me | H | oil | 67 |
| 12ˡ | 4-tert-butylphenyl | 5-fluoro-1,3-phenylene | allyl* | alpha-Me | oil | 70 |
| 13ᵐ | 3-tert-butylphenyl | 5-fluoro-1,3-phenylene | Me | H | oil | 84 |
| 14ⁿ | 3-tert-butylphenyl | 5-fluoro-1,3-phenylene | allyl* | H | oil | 23 |
| 15ᵒ | 3,4-dichlorophenyl | 5-trifluoromethyl-1,3-phenylene | Me | H | oil | 83 |

Notes

* Allyl bromide was used in place of methyl iodide as the alkylating agent.

a. The product gave the following NMR data: (CDCl₃, δ values) 1.7-2.05 (m, 4H), 3.0 (s, 3H), 3.6-4.05 (m, 4H), 6.5-7.0 (m, 3H), 7.2-8.0 (m, 7H).

The 4-[5-fluoro-3-(naphth-2-yloxy)phenyl]-4-hydroxytetrahydropyran used as a starting material was obtained as follows:

Sodium hydride (50% w/w dispersion in mineral oil, 1.2 g) was added portionwise to a mixture of 2-naphthol (3.6 g) and DMA (75 ml) and the mixture was stirred at ambient temperature for 1 hour. 1-Bromo-3,5-difluorobenzene (2.9 g) was added and the mixture was heated to 65° C. for 3 hours. The mixture was cooled to ambient temperature, poured onto a mixture of ice and water and acidified by the addition of 2N hydrochloric acid solution. The mixture was extracted with diethyl ether (3×200 ml). The combined extracts were washed with brine, dried (MgSO₄) and evaporated. The residue was purified by column chromatography using a 1:1 v/v mixture of methylene chloride and petroleum ether (b.p. 40°-60° C.) as eluent. There was thus obtained 3-bromo-5-fluorophenyl 2-naphthyl ether (4.9 g, 62%) as an oil.

Using a similar procedure to that described in the last paragraph of the portion of Note b. below Table III in Example 8 which is concerned with the preparation of starting-materials, a portion (1.59 g) of the product so obtained was reacted with tetrahydropyran-4-one to give the required starting material which was purified by column chromatography using a 9:1 v/v mixture of methylene chloride and diethyl ether as eluent. The material was obtained in 60% yield as an oil.

NMR Spectrum (CDCl$_3$, $\delta$ values) 1.5–2.5 (m, 4H), 3.75–4.0 (m, 4H), 6.6–8.0 (m, 10H).

b. DMF was used in place of THF as the reaction solvent. The product gave the following NMR data: (CDCl$_3$, $\delta$ values) 1.75–2.0 (m, 4H), 3.5–4.0 (m, 6H), 4.9–5.4 (m, 2H), 5.6–6.1 (m, 1H), 6.5–7.0 (m, 3H), 7.1–8.0 (m, 7H).

c. The product gave the following NMR data: (CDCl$_3$, $\delta$ values) 1.20 (d, 3H), 1.5–2.0 (m, 4H), 3.0 (s, 3H), 3.7–4.0 (m, 3H), 6.5–7.0 (m, 3H), 7.1–8.0 (m, 7H).

The (2RS,4SR)-4-[5-fluoro-3-(naphth-2-yloxy)-phenyl]-4-hydroxy-2-methyltetrahydropyran used as a starting material was obtained using the procedures described in the portion of Note a. above which is concerned with the preparation of starting materials except that 2-methyltetrahydropyran-4-one was used in place of tetrahydropyran-4-one. There was thus obtained and separated a mixture of diastereoisomers: the required starting material as a less polar isomer, having the 2-methyl and 4-hydroxy substituents in a trans-relationship, in 17% yield, NMR Spectrum (CDCl$_3$, $\delta$ values) 1.2 (d, 3H), 1.5–2.3 (m, 5H), 3.75–4.1 (m, 3H), 6.5–8.0 (m, 10H); and a (2SR,4SR)-isomer as a more polar isomer, having the 2-methyl and 4-hydroxy substituents in a cis-relationship, in 44% yield, NMR Spectrum (CDCl$_3$, $\delta$ values) 1.2 (d, 3H), 1.6–2.5 (m, 5H), 3.25–3.75 (m, 2H), 3.8–4.2 (m, 1H), 6.5–8.0 (m, 10H).

d. (2RS,4SR)-4-[5-Fluoro-3-(naphth-2-yloxy)phenyl]-4-hydroxy-2-methyl-tetrahydropyran was reacted with ethyl iodide but powdered potassium hydroxide was used in place of sodium hydride and 18-crown-6 was used in place of 15-crown-5.

The product gave the following NMR data: (CDCl$_3$, $\delta$ values) 1.0–1.3 (m, 6H), 1.5–2.2 (m, 4H), 3.0–3.3 (q, 2H), 3.7–4.1 (m, 3H), 6.6–7.0 (m, 3H), 7.1–8.0 (m, 7H).

e. The appropriate (2RS,4SR)-isomer was reacted with allyl bromide but powdered potassium hydroxide was used in place of sodium hydride and 18-crown-6 was used in place of 15-crown-5. The product gave the following NMR data: (CDCl$_3$, $\delta$ values) 1.15 (d, 2H), 1.60–2.10 (m, 4H), 3.50–3.60 (m, 2H), 3.75–4.0 (m, 3H), 4.90–5.30 (m, 2H), 5.6–6.0 (m, 1H), 6.5–7.0 (m, 3H), 7.1–8.0 (m, 7H).

f. Using a similar procedure to that described in Note e. immediately above the appropriate (2SR,4SR)-isomer was reacted with allyl bromide. The product gave the following NMR data: (CDCl$_3$, $\delta$ values) 1.48 (d, 3H), 1.5–2.5 (m, 4H), 3.25–3.75 (m, 4H), 3.8–4.1 (m, 1H), 4.95–5.30 (m, 2H), 5.6–6.0 (m, 1H), 6.6–8.0 (m, 10H).

g. The 4-hydroxy-4-[3-(naphth-2-yloxy)-5-trifluoromethylphenyl]tetrahydropyran used as a starting material was obtained as follows:

The procedures described in the portion of Note a. above which is concerned with the preparation of starting materials were repeated except that 1-bromo-3-fluoro-5-trifluoromethylbenzene was used in place of 1-bromo-3,5-difluorobenzene. There was thus obtained the required starting material in 67% yield as an oil, NMR Spectrum (CDCl$_3$, $\delta$ values) 1.4–1.8 (m, 3H), 1.9–2.3 (m, 2H), 3.7–4.0 (m, 4H), 7.1–7.9 (m, 10H).

h. DMF was used in place of THF as the reaction solvent.

i. The product gave the following NMR data: (CDCl$_3$, $\delta$ values) 1.2 (d, 3H), 1.75–2.1 (m, 4H), 3.0 (s, 3H), 3.65–4.1 (m, 3H), 7.8 (m, 10H).

The (2RS,4SR)-4-hydroxy-2-methyl-4-[3-(naphth-2-yloxy)-5-trifluoromethylphenyl]tetrahydropyran used as a starting material was obtained as follows:

The procedures described in the portion of Note a. above which is concerned with the preparation of starting materials were repeated except that 1-bromo-3-fluoro-5-trifluoromethylbenezene was used in place of 1-bromo-3,5-difluorobenzene and 2-methyltetrahydropyran-4-one was used in place of tetrahydropyran-4-one. There was thus obtained and separated a mixture of diastereoisomers: the required starting material as a less polar isomer in 17% yield, the (2RS,4SR)-isomer, having the 2-methyl and 4-hydroxy substituents in a trans-relationship, NMR Spectrum (CDCl$_3$, $\delta$ values) 1.2 (d, 3H), 1.5–2.3 (m, 5H), 3.75–4.0 (m, 3H), 7.1–8.0 (m, 10H); and a more polar isomer as an oil in 27% yield, the (2SR,4SR)-isomer, having the 2-methyl and 4-hydroxy substituents in a cis-relationship, NMR Spectrum (CDCl$_3$, $\delta$ values) 1.2 (d, 3H), 1.5–2.4 (m, 5H), 3.2–3.6 (m, 2H), 3.8–4.2 (m, 1H), 7.1–8.0 (m, 10H).

j. The product gave the following NMR data: (CDCl$_3$, $\delta$ values) 1.22 (d, 3H), 1.5–2.5 (m, 4H), 2.9 (s, 3H), 3.15–3.6 (m, 2H), 3.8–4.15 (m, 1H), 7.8 (m, 10H).

k. The product gave the following NMR data: (CDCl$_3$, $\delta$ values) 1.3 (s, 9H), 1.8–2.05 (m, 4H), 3.0 (s, 3H), 3.7–4.0 (m, 4H), 6.5–7.5 (m, 7H).

The 4-[5-fluoro-3-(4-tert-butylphenoxy)phenyl]-4-hydroxytetrahydropyran used as a starting material was obtained using the procedures described in the portion of Note a. above which is concerned with the preparation of starting materials except that 4-tert-butylphenol was used in place of 2-naphthol. There was thus obtained the required starting material in 33% yield as an oil, NMR Spectrum (CDCl$_3$, $\delta$ values) 1.25 (s, 9H), 1.55 (s, 1H), 1.6–2.3 (m, 4H), 3.75–4.0 (m, 4H), 6.5–7.8 (m, 7H).

l. DMF was used as the reaction solvent.

The product gave the following NMR data: (CDCl$_3$, $\delta$ values) 1.15 (d, 3H), 1.3 (s, 9H), 1.5–2.1 (m, 4H), 3.5–3.7 (m, 2H), 3.75–4.1 (m, 3H), 5.0–5.4 (m, 2H), 5.6–6.1 (m, 1H), 6.7–7.5 (m, 7H).

The (2RS,4SR)-4-[5-fluoro-3-(4-tert-butylphenoxy)-phenyl]-4-hydroxy-2-methyltetrahydropyran used as a starting material was obtained as follows:

The procedure described in the first paragraph of the portion of Note a. above which is concerned with the preparation of starting materials was repeated except that 4-tert-butylphenol was used in place of 2-naphthol and that 15-crown-5 (10 mg) was added to the reaction mixture with the 1-bromo-3,5-difluorobenzene. There was thus obtained 3-bromo-5-fluorophenyl 4-tert-butylphenyl ether in 65% yield as an oil.

A mixture of the material so obtained (0.65 g), magnesium (0.048 g), a crystal of iodine and THF (2 ml) was briefly heated to reflux and then stirred at ambient temperature for 15 minutes. 2-Methyltetrahydropyran-4-one (0.24 g) was added and the mixture was stirred at ambient temperature for 3 hours. The mixture was partitioned between a saturated aqueous ammonium chloride solution and diethyl ether. The organic phase was washed with brine, dried (MgSO$_4$) and evaporated. The residue, comprising a mixture of diastereoisomers, was purified and the isomers were separated by column chromatography using a 19:1 v/v mixture of methylene chloride and diethyl ether as eluent. There was thus obtained: the required starting material as a less polar isomer in 28% yield as an oil i.e. the (2RS,4SR)-isomer, NMR Spectrum (CDCl$_3$, δ values) 1.42 (d, 3H), 1.55 (s, 9H), 1.7 (s, 1H), 1.5–2.2 (m, 4H), 3.75–4.1 (m, 3H), 6.4–7.5 (m, 7H); and a more polar isomer in 28% yield as an oil i.e. the (2SR,4SR)-isomer.

m. The product gave the following NMR data: (CDCl$_3$, δ values) 1.3 (s, 9H), 1.8–2.05 (m, 4H), 3.0 (s, 3H), 3.6–4.0 (m, 4H), 7.0–7.5 (m, 7H).

The 4-[5-fluoro-3-(3-tert-butylphenoxy)phenyl]-4-hydroxytetrahydropyran used as a starting material was obtained using the procedures described in the portion of Note a. above which is concerned with the preparation of starting materials except that 3-tert-butylphenol was used in place of 2-naphthol. There was thus obtained the required starting material in 68% yield as an oil, NMR Spectrum (CDCl$_3$, δ values), 1.3 (s, 9H), 1.4–1.75 (m, 3H), 1.8–2.3 (m, 2H), 3.7–4.0 (m, 4H), 6.5–7.6 (m, 7H).

n. DMF was used as the reaction solvent in place of THF.

The product gave the following NMR data: (CDCl$_3$, δ values) 1.25 (s, 9H), 1.75–2.1 (m, 4H), 3.5–4.0 (m, 6H), 5.0–5.4 (m, 2H), 5.6–6.1 (m, 1H), 6.4–7.3 (m, 7H).

o. Sodium hydride (55% w/w dispersion in mineral oil, 0.045 g) was added portionwise to a mixture of 4-[3-(3,4-dichlorophenoxy)-5-trifluoromethylphenyl]-4-hydroxytetrahydropyran (0.38 g) and DMF (3 ml) which had been cooled to −10° C. for 30 minutes. A solution of methyl iodide (0.156 g) in THF (1 ml) was added and the mixture was stirred at ambient temperature for 1.5 hours. The mixture was poured onto ice, acidified by the addition of dilute hydrochloric acid solution, and extracted with ethyl acetate. The organic phase was washed with brine, dried (MgSO$_4$) and evaporated. The residue was purified by column chromatography using a 10:1 v/v mixture of toluene and ethyl acetate as eluent. There was thus obtained the required product which gave the following NMR data: (CD$_3$SOCD$_3$, δ values) 1.9–2.0 (m, 4H), 2.9 (s, 3H), 3.7 (m, 4H), 7.4–7.5 (m, 3H), 7.1 (m, 1H), 7.4 (m, 1H), 7.7 (d, 1H).

The 4-[3-(3,4-dichlorophenoxy)-5-trifluoromethylphenyl]-4-hydroxytetrahydropyran used as a starting material was obtained using the procedures described in the portion of Note a. above which is concerned with the preparation of starting materials except that 3,4-dichlorophenol was used in place of 2-naphthol and 1-bromo-3-fluoro-5-trifluoromethylbenzene was used in place of 1-bromo-3,5-difluorobenzene. There was thus obtained the required starting material in 30% yield as an oil.

NMR Spectrum (CD$_3$SOCD$_3$, δ values) 1.4–2.1 (m, 4H), 3.65–3.9 (m, 4H), 5.35 (s, 1H), 7.05–7.7 (m, 6H).

EXAMPLE 11

The procedure described in Example 3 was repeated except that 4-[5-fluoro-3-(naphth-2-yloxy)phenyl]-4-hydroxy-2,2-dimethyltetrahydropyran was used in place of 4-hydroxy-4-[3-(naphth-2-ylsulphonyl)phenyl]-tetrahydropyran, 15-crown-5 (0.1 equivalents) was added to the reaction mixture after the addition of the methyl iodide, and the reaction mixture was stirred at ambient temperature for 2 days. There was thus obtained 4-[5-fluoro-3-(naphth-2-yloxy)phenyl]-4-methoxy-2,2-dimethyltetrahydropyran in 97% yield as an oil.

NMR Spectrum (CDCl$_3$, δ values) 1.20 (s, 3H), 1.45 (s, 3H), 1.75–2.1 (m, 4H), 2.95 (s, 3H), 3.55–4.20 (m, 2H), 6.5–8.0 (m, 10H).

The 4-[5-fluoro-3-(naphth-2-yloxy)phenyl]-4-hydroxy-2,2-dimethyltetrahydropyran used as a starting material was obtained as follows:

A mixture of 2,3-dihydro-2,2-dimethylpyran-4-one (2.72 g, J. Org. Chem., 1963, 687), 10% palladium-on-charcoal catalyst (0.27 g) and ethanol (80 ml) was stirred under an atmosphere of hydrogen for 6 hours. The mixture was filtered and the filtrate was evaporated. There was thus obtained 2,2-dimethyltetrahydropyran-4-one (2.05 g, 74%), as a liquid.

IR Spectrum 1730 cm$^{-1}$ (C=O).

Using a similar procedure to that described in the last paragraph of the portion of Note b. below Table III in Example 8 which is concerned with the preparation of starting materials, the organo-lithium derivative from 3-bromo-5-fluorophenyl 2-naphthyl ether was reacted with 2,2-dimethyltetrahydropyran-4-one to give the required starting material in 68% yield as an oil, NMR Spectrum (CDCl$_3$, δ values) 1.25 (s, 3H), 1.50 (s, 3H), 1.75 (s, 1H), 1.8–2.5 (m, 4H), 3.75–4.25 (m, 2H), 6.5–8.0 (m, 10H).

EXAMPLE 12

A mixture of 4-bromoiodobenzene (0.8 g), 4-(3-mercaptophenyl)-4-methoxytetrahydropyran (0.5 g), cuprous chloride (0.5 g), potassium carbonate (0.4 g) and DMF (0.5 ml) was heated to 140° C. for 45 minutes. The mixture was cooled to ambient temperature and partitioned between diethyl ether and water. The organic phase was washed with water and with brine, dried (MgSO$_4$) and evaporated. The residue was purified by column chromatography using increasingly polar mixtures of hexane and ethyl acetate as eluent. There was thus obtained 4-[3-(4-bromophenylthio)phenyl]-4-methoxytetrahydropyran (0.4 g, 47%), m.p, 91°–93° C.

NMR Spectrum (CDCl$_3$, δ values) 1.75 (m, 4H), 2.75 (s, 3H), 3.6 (m, 4H), 6.9–7.2 (m, 8H).

The 4-(3-mercaptophenyl)-4-methoxytetrahydropyran used as a starting material was obtained as follows:

A solution of 4-(3-bromophenyl)-4-methoxytetrahydropyran (1 g) in THF (4 ml) was cooled to −80° C. under an atmosphere of argon and n-butyl-lithium (1.6M in hexane, 2.4 ml) was added dropwise. The mixture was stirred at −80° C. for 30 minutes, sulphur (0.12 g) was added and the mixture was stirred at −80° C. for a further 30 minutes. Water (10 ml) was added and the mixture was allowed to warm to ambient temperature. The mixture was extracted with diethyl ether (10 ml). The aqueous phase was acidified to pH 4 by the addition of dilute aqueous hydrochloric acid solution and extracted with diethyl ether (2×10 ml). The combined organic extracts were dried (MgSO$_4$) and evaporated. There was thus obtained the required starting material as an oil (0.5 g) which crystallised on standing and was used without further purification.

EXAMPLE 13

Using a similar procedure to that described in Example 12, except that, unless otherwise stated, the appropriate iodobenzene was used in place of 4-bromoiodobenzene, there were obtained the compounds described in the following table:

TABLE VI

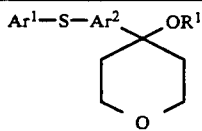

Ex. 13.

| Compd. No. | Ar¹ | Ar² | R¹ | m.p. (°C.) | Yield (%) |
|---|---|---|---|---|---|
| 1[a] | 4-biphenylyl | 1,3-phenylene | Me | oil | 17 |
| 2[b] | 3-biphenylyl | 1,3-phenylene | Me | oil | 34 |
| 3[c] | 4-isopropyl-phenyl | 1,3-phenylene | Me | oil | 78 |
| 4[d] | 4-isopropoxy-phenyl | 1,3-phenylene | Me | oil | 45 |
| 5[e] | 4-(2,2,2-trifluoro-ethoxy)phenyl | 1,3-phenylene | Me | 126–128 | 42 |
| 6[f] | 3-(2,2,2-trifluoro-ethoxy)phenyl | 1,3-phenylene | Me | oil | 54 |
| 7[g] | 3-(2-cyanoprop-2-yl)phenyl | 1,3-phenylene | Me | oil | 24 |
| 8[h] | 3-chloro-4-(2-cyano-prop-2-yl)-phenyl | 1,3-phenylene | Me | oil | 51 |
| 9[i] | 3-(2-methyl-sulphonyl-prop-2-yl)-phenyl | 1,3-phenylene | Me | oil | 20 |
| 10[j] | 4-acetamido-phenyl | 1,3-phenylene | Me | 162–164 | 48 |

Notes a. The aryl halide used was 4-bromobiphenyl. The product gave the following NMR data (CDCl₃, δ values) 1.95 (m, 4H), 3.0 (s, 3H), 3.8 (m, 4H), 7.25–7.60 (m, 13H).

b. The aryl halide used was 3-bromobiphenyl. The product gave the following NMR data (CDCl₃, δ values) 1.95 (m, 4H), 2.95 (s, 3H), 3.8 (m, 4H), 7.2–7.6 (m, 13H).

c. The product gave the following NMR data (CDCl₃, δ values) 1.25 (d, 6H), 1.95 (m, 4H), 2.96 (s, 3H), 2.96 (m, 1H), 3.8 (m, 4H), 7.1–7.35 (m, 8H).

d. The product gave the following NMR data (CDCl₃, δ values), 1.35 (d, 6H), 1.95 (m, 4H), 2.95 (s, 3H), 3.7 (m, 4H), 4.55 (m, 1H), 6.7–7.4 (m, 8H).

The 4-isopropoxyiodobenzene used as a starting material was obtained as follows:

A mixture of 4-hydroxyiodobenzene (4 g), isopropyl bromide (3 g), potassium carbonate (2.5 g) and DMF (20 ml) was heated to 100° C. for 6 hours. The mixture was cooled, poured into water (80 ml) and extracted with diethyl ether (50 ml). The organic phase was dried (MgSO₄) and evaporated to give the required starting material as a liquid which was used without further purification.

e. The product gave the following NMR data: (CDCl₃, δ values) 1.95 (m, 4H), 2.95 (s, 3H), 3.8 (m, 4H), 4.38 (q, 2H), 6.9–7.4 (m, 8H).

The 4-(2,2,2-trifluoroethoxy)iodobenzene used as a starting material was obtained by the reaction of 4-hydroxyiodobenzene with 2,2,2-trifluoroethyl bromide using similar conditions to those described in Note d. immediately above.

f. The product gave the following NMR data: (CDCl₃, δ values) 1.95 (m, 4H), 2.95 (s, 3H), 3.8 (m, 4H), 4.3 (q, 2H), 6.8–7.0 (m, 3H), 7.2–7.5 (m, 5H).

The 3-(2,2,2-trifluoroethoxy)iodobenzene used as a starting material was obtained by the reaction of 3-hydroxyiodobenzene with 2,2,2-trifluoroethyl bromide using similar conditions to those described in Note d. immediately above.

g. The product gave the following NMR data: (CDCl₃, δ values) 1.7 (s, 6H), 1.9–2.1 (m, 4H), 2.97 (s, 3H), 3.75–3.90 (m, 4H), 7.2–7.45 (m, 8H).

The required iodobenzene starting material was obtained as follows:

Using similar procedures to those described within Note b. below Table II in Example 4, but using 3-methyliodobenzene in place of 3-bromo-5-trifluoromethylphenyl 4-tolyl sulphide as a starting material, there was obtained 3-(2-cyanoprop-2-yl)iodobenzene in 66% yield as an oil.

NMR Spectrum (CDCl₃, δ values) 1.7 (s, 6H), 7.06–7.16 (t, 1H), 7.44–7.48 (d, 1H), 7.54–7.58 (d, 1H), 7.7 (t, 1H).

h. The product gave the following NMR data: (CDCl₃, δ values) 1.46 (s, 6H), 1.54–1.65 (m, 4H), 2.0 (s, 3H), 3.44–3.49 (m, 4H), 6.72–6.76 (d, 1H), 6.89 (s, 1H), 6.97–7.03 (m, 4H), 7.13 (s, 1H).

The 3-chloro-4-(2-cyanoprop-2-yl)iodobenzene used as a starting material was obtained as follows:

A mixture of 3-chloro-4-methyliodobenzene (9.0 g), N-bromosuccinimide (8.5 g), benzoyl peroxide (0.3 g) and carbon tetrachloride (80 ml) was stirred and heated to reflux for 3 hours. The mixture was cooled to ambient temperature and filtered. The filtrate was evaporated to give 4-bromomethyl-3-chloroiodobenzene (11 g) which was used without further purification.

A mixture of a portion (7.2 g) of the product so obtained, potassium cyanide (4.1 g), tetrabutylammonium bromide (0.33 g) methylene chloride (20 ml) and water (20 ml) was stirred and heated to reflux for 4 hours. The mixture was cooled to ambient temperature and the organic phase was separated, washed with water and with brine, dried (MgSO₄) and evaporated. The residue was purified by column chromatography using methylene chloride as eluent. There was thus obtained 4-cyanomethyl-3-chloroiodobenzene (1.8 g).

NMR Spectrum (CDCl₃, δ values) 3.77 (s, 2H) 7.25–7.26 (d, 1H), 7.63–7.68 (d, 1H), 7.77–7.89 (d, 1H).

A mixture of the product so obtained, methyl iodide (2.0 ml) and DMF (15 ml) was added to a suspension of sodium hydride (55% w/w dispersion in mineral oil; 0.51 g) in DMF (10 ml) which was cooled to 5° C. The mixture was stirred at 5° C. for 15 minutes and then allowed to warm to ambient temperature. The mixture was poured into a mixture of ice and water and extracted with ethyl acetate (3×50 ml). The combined extracts were washed with water and brine, dried (MgSO₄) and evaporated. The residue was purified by column chromatography using methylene chloride as eluent to give the required starting material (1.27 g, 64%).

NMR Spectrum (CDCl₃, δ values) 1.85 (s, 6H), 7.17–7.23 (d, 1H), 7.6–7.66 (d, 1H), 7.8 (s, 1H).

i. The product gave the following NMR data: (CDCl₃, δ values) 0.8 (s, 6H), 1.92–2.05 (m, 4H), 2.52 (s, 3H), 2.95 (s, 3H), 3.75–3.95 (m, 4H), 7.2–7.6 (m, 8H).

The 3-(2-methylsulphonylprop-2-yl)iodobenzene used as a starting material was obtained as follows:

A solution of sodium hydroxide (1.75 g) in water (10 ml) was added to a mixture of 3-bromomethyliodobenzene (3.25 g), S-methylisothiouronium sulphate (3.04 g) and DMF (20 ml) and the mixture was stirred at ambient temperature for 2 hours. The mixture was partitioned between diethyl ether and water. The organic phase was washed with water and with brine, dried (MgSO4) and evaporated. There was thus obtained 3-methylthiomethyliodobenzene (3.1 g).

A solution of potassium peroxymonosulphate (12 g) in water (25 ml) was added to a solution of the product so obtained in ethanol (100 ml) and the mixture was stirred at ambient temperature for 16 hours. The mixture was evaporated and the residue was partitioned between ethyl acetate and water. The organic phase was washed with water and with brine, dried (MgSO4) and evaporated. There was thus obtained 3-methylsulphonylmethyliodobenzene (2.2 g).

NMR Spectrum 2.78 (s, 3H), 4.17 (s, 2H), 7.1–7.2 (m, 1H), 7.38–7.42 (d, 1H), 7.73–7.77 (m, 2H).

Using a similar procedure to that described in the last paragraph of Note h. immediately above the product so obtained was reacted with methyl iodide to give the required starting material in 56% yield, m.p. 124° C. (recrystallised from a mixture of hexane and ethyl acetate).

j. The product gave the following NMR data: (CDCl3, δ values) 1.85–2.05 (m, 4H), 2.16 (m, 3H), 2.75 (m, 3H), 3.75–3.9 (m, 4H), 7.7–7.55 (m, 8H).

EXAMPLE 14

A solution of potassium peroxymonosulphate (0.4 g) in water (1 ml) was added to a mixture of 4-allyloxy-4-[3-(naphth-2-ylthio)phenyl]tetrahydropyran (0.2 g) and ethanol (2.5 ml) and the resultant mixture was stirred at ambient temperature for 18 hours. The mixture was partitioned between chloroform and water. The organic phase was dried (MgSO4) and evaporated. The residue was purified by column chromatography using increasingly polar mixtures of hexane and ethyl acetate as eluent. There was thus obtained 4-allyloxy-4-[3-(naphth2-ylsulphonyl)phenyl]tetrahydropyran (0.12 g, 55%), m.p. 142°–144° C.

NMR Spectrum (CDCl3, δ values) 1.95 (m, 4H)), 3.5 (m, 2H), 3.85 (m, 4H), 5.08 (m, 1H), 5.2 (m, 1H), 5.8 (m, 1H), 7.4–7.7 (m, 4H), 7.8–8.1 (m, 6H), 8.6 (s, 1H).

EXAMPLE 15

Using a similar procedure to that described in Example 7 or in Example 14, except that the appropriate sulphide was used in place of 4-methoxy-4-[3-(naphth-2-ylthio)-5-trifluoromethylphenyl]tetrahydropyran or 4-allyloxy-4-[3-(naphth-2-ylthio)phenyl]tetrahydropyran respectively, there were obtained the compounds described in the following table:

TABLE VII

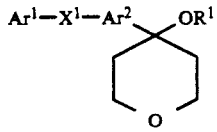

| Ex. 15. Compd. No. | Ar¹ | X¹ | Ar² | R¹ | m.p. (°C.) | Yield (%) |
|---|---|---|---|---|---|---|
| 1ᵃ | 4-tert-butyl-phenyl | SO | 1,3-phenylene | Me | 112–114 | 52 |
| 2ᵇ | 4-tert-butyl-phenyl | SO₂ | 1,3-phenylene | Me | 115–120 | 33 |
| 3ᶜ | 3,4-dichloro-phenyl | SO₂ | 1,3-phenylene | Me | 120–122 | 33 |
| 4ᵈ | 3-biphenylyl | SO₂ | 1,3-phenylene | Me | oil | 77 |
| 5ᵉ | 3-(2,2,2-trifluoroethoxy)phenyl | SO₂ | 1,3-phenylene | Me | 90–93 | 76 |

Notes a. The product gave the following NMR data: (CDCl3, δ values) 1.5 (s, 9H), 1.9–2.05 (m, 4H), 2.92 (s, 3H), 3.78–3.90 (m, 4H), 7.45–7.60 (m, 7H), 7.7 (m, 1H).

b. The product gave the following NMR data: (CDCl3, δ values) 1.8 (m, 9H), 1.9–2.1 (m, 4H), 2.95 (m, 3H), 3.8–3.9 (m, 4H), 7.48–7.6 (m, 4H), 7.82–7.90 (m, 3H), 7.98 (m, 1H).

c. The product was recrystallised from a mixture of hexane and ethyl acetate and gave the following NMR data: (CDCl3, δ values) 1.9–2.08 (m, 4H), 2.95 (s, 3H), 3.8–3.9 (m, 4H), 7.5–7.7 (m, 3H), 7.75–7.9 (m, 2H), 7.95–8.05 (m, 2H).

d. The product gave the following NMR data: (CDCl3, δ values) 2.0 (m, 4H), 2.95 (s, 3H), 3.85 (m, 4H), 7.3–8.2 (m, 13H).

e. The product gave the following NMR data: (CDCl3, δ values) 2.0 (m, 4H), 2.95 (s, 3H), 3,85 (m, 4H), 4.4 (q, 2H), 7.1–8.0 (m, 8H).

EXAMPLE 16

A solution of 4-[3-(4-bromophenylthio)phenyl]-4-methoxytetrahydropyran (0.4 g) in THF (3 ml) was cooled to −80° C. and n-butyl lithium (1.6 m in hexane, 0.7 ml) was added dropwise. the mixture was stirred at −80° C. for 30 minutes and diethyl ketone (0.27 g) was added. The resultant mixture was stirred and allowed to warm to ambient temperature. The mixture was poured into brine (10 ml) and extracted with diethyl ether. The organic phase was dried (MgSO4) and evaporated. The residue was purified by column chromatography using increasingly polar mixtures of hexane and ethyl acetate as eluent. There was thus obtained 4-[3-(4-(3-hydroxypent-3-yl)phenylthio)phenyl]-4-methoxytetrahydropyran (0.3 g, 74%), as a colourless oil.

NMR Spectrum (CDCl3, δ values) 0.8 (t, 6H), 1.7–2.0 (m, 8H), 2.95 (s, 3H), 3.8 (m, 4H), 7.2–7.4 (m, 8H).

EXAMPLE 17

The procedure described in Example 16 was repeated except that acetone was used in place of diethyl ketone. There was thus obtained 4-[3-(4-(2-hydroxyprop-2-yl)phenylthio)phenyl]-4-methoxytetrahydropyran in 40% yield as an oil.

NMR Spectrum (CDCl3, δ values) 1.38 (s, 6H), 1.5 (broad s, 1H), 1.75 (m, 4H), 2.7 (s, 3H), 3.6 (m, 4H), 7.0–7.3 (m, 8H).

EXAMPLE 18

Sodium hydride (60% w/w dispersion in mineral oil, 0.032 g) was added portionwise to a solution of 4-[3-(4-acetamidophenylthio)phenyl]-4-methoxytetrahydropyran (0.2 g) in DMF (1 ml) and the mixture was stirred at ambient temperature for 1 hour. Methyl iodide (0.1 ml) was added and the mixture was stirred at ambient temperature for 30 minutes. The mixture was partitioned between ethyl acetate and water. The organic phase was washed with water and with brine, dried (MgSO$_4$) and evaporated. The residue was purified by column chromatography using increasingly polar mixtures of hexane and ethyl acetate as eluent. There was thus obtained 4-methoxy-4-[3-(4-N-methylacetamidophenylthio)phenyl]tetrahydropyran (0.16 g, 78%), as an oil.

NMR Spectrum (CDCl$_3$, δ values) 1.85-2.1 (m, 7H), 2.98 (s, 3H), 3.27 (s, 3H), 3.78-3.9 (m, 4H), 7.05-7.45 (m, 8H).

EXAMPLE 19

Using a similar procedure to that described in Example 12, 6-bromo-2-naphthalenethiol was reacted with 4-(3-iodophenyl)-4-methoxytetrahydropyran to give 4-[3-(6-bromonaphth-2-ylthio)phenyl]-4-methoxytetrahydropyran in 30% yield, as an oil.

NMR Spectrum (CDCl$_3$, δ values) 1.85-2.1 (m, 4H), 2.95 (m, 3H), 3.75-3.9 (m, 4H), 7.25-7.78 (m, 9H), 7.96 (m, 1H).

The 6-bromo-2-naphthalenethiol used as a starting material was obtained as follows:

Sodium hydride (60% w/w dispersion in mineral oil, 0.9 g) was added portionwise to a mixture of 6-bromo-2-naphthol (5 g) and DMF (40 ml) and the mixture was stirred at ambient temperature for 1 hour. N,N-Dimethylthiocarbamoyl chloride (4.8 g) was added dropwise and the mixture was stirred at ambient temperature for 30 minutes. The mixture was partitioned between diethyl ether and water. The organic phase was washed with water and with brine, dried (MgSO$_4$) and evaporated. The residue was purified by column chromatography using increasingly polar mixtures of hexane and chloroform as eluent. There was thus obtained 6-bromo-2-(N,N-dimethylthiocarbamoyl)naphthalene (3.7 g, 53%) as a solid.

A portion (0.8 g) of the material so obtained was heated to 250° C. for 5.5 hours. The reaction product was cooled to ambient temperature. Ethanol (10 ml) and aqueous sodium hydroxide solution (10% w/v, 3 ml) were added and the solution was heated to reflux for 2.5 hours. The mixture was cooled to ambient temperature, water (10 ml) was added and the mixture was acidified to pH 1 by the addition of concentrated hydrochloric acid. The mixture was extracted with chloroform. The organic phase was dried (MgSO$_4$) and evaporated to give the required thiol starting material (0.3 g, 49%).

NMR Spectrum (CDCl$_3$, δ values), 7.35 (m, 1H), 7.5-7.75 (m, 5H), 7.95 (m, 1H).

The 4-(3-iodophenyl)-4-methoxytetrahydropyran used as a starting material was obtained by repetition of the procedures described in the portion of Example 1 which is concerned with the preparation of starting materials except that 1,3-di-iodobenzene was used in place of 1,3-dibromobenzene. There was thus obtained the required starting material in 48% yield, m.p 47°–49° C.

NMR Spectrum (CDCl$_3$, δ values) 1.88-2.1 (m, 4H), 3.0 (s, 3H), 3.78-3.95 (m, 4H), 7.1 (d of d's, 1H), 7.35 (m, 1H), 7.62 (m, 1H), 7.73 (m, 1H).

EXAMPLE 20

A solution of 4-[3-(4-bromophenylthio)phenyl]-4-methoxytetrahydropyran (0.3 g) in THF (3 ml) was cooled to −80° C. and n-butyl-lithium (1.2M in hexane, 0.7 ml) was added dropwise. The mixture was stirred at −80° C. for 30 minutes, trimethylsilyl chloride (0.1 g) was added and the mixture was stirred and allowed to warm to ambient temperature. The mixture was partitioned between diethyl ethyl and water. The organic phase was dried (MgSO$_4$) and evaporated. The residue was purified by column chromatography using increasingly polar mixtures of hexane and ethyl acetate as eluent. There was thus obtained 4-methoxy-4-[3-(4-trimethylsilylphenylthio)phenyl]tetrahydropyran (0.2 g, 60%), as an oil.

NMR Spectrum (CDCl$_3$, δ values) 0.05 (s, 9H), 1.8 (m, 4H), 2.8 (s, 3H), 3.65 (m, 4H), 7.1-7.3 (m, 8H).

EXAMPLE 21

Sodium hydride (60% w/w dispersion in mineral oil, 0.3 g) was added portionwise to a solution of 4-[3-(4-(2-hydroxyprop-2-yl)phenylthio)phenyl]-4-methoxytetrahydropyran (0.13 g) in DMF (2 ml) and the mixture was stirred at ambient temperature for 15 minutes. Methyl iodide (0.11 ml) was added and the mixture was stirred at ambient temperature for 18 hours. The mixture was partitioned between diethyl ether and water. The organic phase was dried (MgSO$_4$) and evaporated. The residue was purified by column chromatography using increasingly polar mixtures of hexane and ethyl acetate as eluent. There was thus obtained 4-methoxy-4-[3-(4-(2-methoxyprop-2-yl)phenylthio)phenyl]tetrahydropyran (0.05 g, 40%) as an oil.

NMR Spectrum (CDCl$_3$, δ values) 1.5 (s, 6H), 1.85-2.08 (m, 4H), 2.95 (s, 3H), 3.08 (s, 3H), 3.75-3.9 (m, 4H), 7.2-7.4 (m, 8H).

EXAMPLE 22

A mixture of 4-[5-bromo-3-(4-tert-butylphenylthio)phenyl]-4-methoxytetrahydropyran (0.35 g), potassium cyanide (0.116 g), calcium hydroxide (0.01 g), palladium (II) acetate (0.028 g), triphenylphosphine (0.07 g) and DMF (3 ml) was heated to 100° C. for 30 minutes and then to 140° C. for 5 hours. A second portion of palladium (II) acetate (0.037 g) was added and the mixture was heated to 140° C. for 4 hours. The mixture was cooled to ambient temperature and partitioned between diethyl ether and water. The organic phase was dried (MgSO$_4$) and evaporated. The residue was purified by column chromatography using increasingly polar mixtures of hexane and ethyl acetate as eluent. There was thus obtained 4-[5-cyano-3-(4-tert-butylphenylthio)phenyl]-4-methoxytetrahydropyran (0.09 g, 29%), as an oil.

NMR Spectrum (CDCl$_3$, δ values) 1.45 (s, 9H), 1.75-2.0 (m, 4H), 2.95 (s, 3H), 3.78-3.85 (m, 4H), 7.25 (m, 1H), 7.35-7.5 (m, 6H).

EXAMPLE 23

Using similar procedure to that described in Example 12, 2-chloro-4-iodoacetanilide was reacted with 4-(3-mercaptophenyl)-4-methoxytetrahydropyran to give 4-[3-(4-acetamido-3-chlorophenylthio)phenyl] -4-methoxytetrahydropyran in yield as an oil.

NMR Spectrum (CDCl$_3$, δ values) 1.88–2.05 (m, 4H), 2.25 (s, 3H), 2.95 (s, 3H), 3.75–3.9 (m, 4H), 7.18–7.42 (m, 6H), 8.35 (m, 1H).

The 2-chloro-4-iodoacetanilide used as a starting material was obtained as follows:

Acetyl chloride (0.56 ml) was added dropwise to a mixture of 2-chloro-4-iodoaniline (2 g), pyridine (0.67 ml) and methylene chloride (20 ml) which had been cooled in an ice bath. The mixture was stirred at 0° C. for 10 minutes. The mixture was partitioned between methylene chloride and water. The organic phase was dried (MgSO$_4$) and evaporated. The residue was recrystallised from a mixture of hexane and ethyl acetate. There was thus obtained the required starting material (1.6 g), m.p. 142°–146° C.

EXAMPLE 24

Using a similar procedure to that described in Example 18, 4-[3-(4-acetamido-3-chlorophenylthio)phenyl]-4-methoxytetrahydropyran was reacted with methyl iodide to give 4-[3-(3-chloro-4-N-methylacetamidophenylthio)phenyl]-4-methoxytetrahydropyran in 77% yield as an oil.

NMR Spectrum (CDCl$_3$, δ values) 1.82 (s, 3H), 1.9–2.1 (m, 4H), 3.0 (s, 3H), 3.18 (s, 3H), 3.8–3.92 (m, 4H), 7.15 (m, 2H), 7.28 (m, 1H), 7.42 (m, 3H), 7.55 (m, 1H).

EXAMPLE 25

Using a similar procedure to that described in Example 12, 2'-chloro-4'-iodo-2,2,2-trifluoro-N-methylacetanilide was reacted with 4-(3-mercaptophenyl)-4-methoxytetrahydropyran to give 4-[3-(3-chloro-4-(N-methyltrifluoroacetamido)phenylthio)-phenyl]-4-methoxytetrahydropyran in 8% yield as a gum.

NMR Spectrum (CDCl$_3$, δ values) 1.9–2.0 (m, 4H), 2.95 (s, 3H), 3.28 (s, 3H), 3.8–3.95 (m, 4H), 7.1 (m, 1H), 7.18 (m, 1H), 7.27 (m, 1H), 7.42 (m, 3H), 7.53 (m, 1H).

There was also obtained as a by-product 4-[3-(4-amino-3-chlorophenylthio)phenyl]-4-methoxytetrahydropyran in 29% yield as a NMR Spectrum (CDCl$_3$, δ values) 1.85–2.05 (m, 4H), 2.95 (s, 3H), 3.7–3.9 (m, 4H), 6.75 (d, 1H), 7.05 (m, 1H), 7.15–7.3 (m, 4H), 7.42 (d, 1H).

The 2'-chloro-4'-iodo-2,2,2-trifluoro-N-methylacetanilide used as a starting material was obtained from 2-chloro-4-iodaniline by acylation with trifluoroacetyl chloride using the procedure described in the portion of Example 23 which is concerned with the preparation of starting materials to give 2'-chloro-4'-iodo-2,2,2-trifluoroacetanilide in 50% yield, NMR Spectrum (CDCl$_3$, δ values) 7.68 (d of d, 1H), 7.8 (d, 1H), 9.0 (d, 1H), and by methylation of that product using the procedures described in Example 18. There was thus obtained the required starting material in 60% yield, m.p. 51°–52° C. (recrystallised from hexane).

EXAMPLE 26

Using a similar procedure to that described in Example 12, except that the appropriate iodobenzene was used in place of 4-bromoiodobenzene, there were obtained the compounds described in the following table:

TABLE VIII

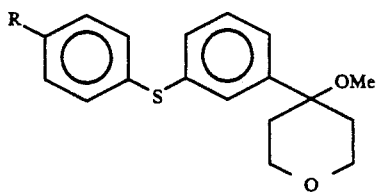

| Ex. 26 Compd. No. | R | m.p. (°C.) | Yield (%) |
|---|---|---|---|
| 1[a] | isobutyryl | oil | 50 |
| 2[b] | trifluoroacetyl | gum | 30 |
| 3[c] | benzoyl | oil | 60 |
| 4[d] | 4-chlorobenzoyl | 137–139 | 50 |
| 5[e] | 2-oxopyrrolidinyl | 84–87 | 35 |
| 6[f] | acetyl | oil | 52 |

NOTES a. The product gave the following NMR data (CDCl$_3$, δ values) 1.2 (d, 6H), 1.9–2.1 (m, 4H), 3.0 (s, 3H), 3.5 (m, 1H), 3.8–4.0 (m, 4H), 7.2–7.9 (m, 8H).

The 4-iodoisobutyrophenone used as a starting material was obtained as follows:

A solution of 1,4-diiodobenzene (3.3 g) in THF (20 ml) was cooled to −80° C. and n-butyl-lithium (1.6M in hexane, 6.5 ml) was added dropwise. The mixture was stirred at −80° C. for 30 minutes. Isobutyraldehyde (1 ml) was added and the mixture was stirred at −80° C. for 30 minutes and then allowed to warm to ambient temperature. The mixture was partitioned between diethyl ether and water. The organic phase was washed with water, dried (MgSO$_4$) and evaporated.

A mixture of the residue so obtained, pyridinium chlorochromate (1.9 g) and methylene chloride (20 ml) was stirred at ambient temperature for 2 hours. Diethyl ether (60 ml) was added and the mixture was filtered. The filtrate was evaporated and the residue was purified by column chromatography using increasingly polar mixtures of hexane and ethyl acetate as eluent. There was thus obtained the required starting material as a yellow oil (1.4 g).

NMR Spectrum (CDCl$_3$, δ values) 1.2 (d, 3H), 3.5 (m, 1H), 7.65 (d, 2H), 7.8 (d, 2H).

b. The product gave the following NMR data (CDCl$_3$, δ values) 1.9–2.1 (m, 4H), 3.0 (s, 3H), 3.8–3.92 (m, 4H), 7.2 (m, 2H), 7.48 (m, 3H), 7.60 (m, 1H), 7.9 (m, 2H).

The 4'-bromo-2,2,2-trifluoroacetophenone which was used as an appropriate starting material has been described in *J. Organomet. Chem*, 1983, 251, 139.

c. The product gave the following NMR data (CDCl$_3$, δ values) 1.9–2.1 (m, 4H), 3.0 (s, 3H), 3.8–4.0 (m, 4H), 7.2–7.8 (m, 13H).

The 4-iodobenzophenone used as a starting material has been described in *J.C.S. Perkin I*, 1973, 2940.

d. The 4-chloro-4'iodobenzophenone used as a starting material was obtained as described in *J. Chem. Soc.*, 1961, 1405.

e. The N-(4-iodophenyl)pyrrolidin-2-one used as a starting material was obtained as follows:

Iodine monochloride (4 g) was added to a mixture of N-phenylpyrrolidin-2-one (2 g) and glacial acetic acid (10 ml) and the mixture was heated to 90° C. for 1.5 hours. The mixture was cooled to ambient temperature and partitioned between diethyl ether and water. The organic phase was washed with water, dried (MgSO$_4$)

and evaporated. There was thus obtained the required starting material (2 g), m.p. 136°–138° C. (recrystallised from a mixture of hexane and ethyl acetate).

f. The product gave the following NMR data (CDCl$_3$, δ values) 1.9–2.1 (m, 4H), 2.58 (s, 3H), 2.98 (s, 3H), 3.78–3.94 (m, 4H), 7.23 (m, 2H), 7.42 (m, 3H), 7.55 (m, 1H), 7.85 (m, 2H).

The 4-iodoacetophenone used as a starting material has been described in *J. Amer. Chem. Soc.*, 69, 2141.

EXAMPLE 27

Using a similar procedure to that described in Example 12, 5-iodo-1,1,3,3-tetramethyl-1,3-dihydrobenzo[c]-thiophene-2,2-dioxide was reacted with 4-(3-mercapto-phenyl)-4-methoxytetrahydropyran to give 4-methoxy-4-[3-(1,1,3,3-tetramethyl-2,2-dioxo-1,3-dihydroben-zo[c]thien-5-ylthio)phenyl]tetrahydropyran in 28% yield, m.p. 133°–135° C.

NMR Spectrum (CDCl$_3$, δ values) 1.6 (d, 12H), 1.9–2.1 (m, 4H), 2.95 (s, 3H), 3.8–4.0 (m, 4H), 7.1–7.5 (m, 7H).

The 5-iodo-1,1,3,3-tetramethyl-1,3-dihydrobenzo[c]-thiophene-2,2-dioxide used as a starting material was obtained as follows:

Potassium peroxymonosulphate (110 g) was added portionwise to a mixture of 1,3-dihydrobenzo[c]thio-phene (23 g; *J. Amer. Chem. Soc.*, 81, 4266), ethanol (400 ml) and water (300 ml) and the mixture was stirred at ambient temperature for 18 hours. Water (400 ml) was added and the mixture was extracted with chloroform (3×100 ml). The combined organic extracts were washed with water, dried (MgSO$_4$) and evaporated. The residue was recrystallised from ethyl acetate to give 1,3-dihydrobenzo[c]thiophene-2,2-dioxide (17 g).

NMR Spectrum (CDCl$_3$, δ values) 4.35 (s, 4H), 7.2–7.4 (m, 4H).

Sodium hydride (60% w/w dispersion in mineral oil; 6 g) was added portionwise to a mixture of a portion (5 g) of the product so obtained and DMF (70 ml). The mixture was stirred at ambient temperature for 30 minutes. Methyl iodide (35 g) was added and the mixture was stirred at ambient temperature for 3 hours. The mixture was partitioned between diethyl ether and water. The organic layer was washed with water, dried (MgSO$_4$) and evaporated. The residue was recrystallised from ethyl acetate to give 1,1,3,3-tetramethyl-1,3-dihydrobenzo[c]thiophene-2,2-dioxide as an oil (6 g).

NMR Spectrum (CDCl$_3$, δ values) 1.65 (s, 12H), 7.25 (m, 2H), 7.4 (m, 2H).

Iodine (0.3 g) was added to a mixture of a portion (0.6 g) of the product so obtained, iodic acid (0.1 g), concentrated sulphuric acid (0.3 ml), water (0.3 ml) and acetic acid (2 ml) and the mixture was heated to 95° C. for 3 hours. The mixture was cooled to ambient temperature then water (10 ml) and sufficient aqueous sodium sulphate solution to discharge the excess of iodide were added in turn. The mixture was extracted with diethyl ether. The organic phase was washed with water, dried (MgSO$_4$) and evaporated. The residue was purified by column chromatography on reversed-phase silica using decreasingly polar mixtures of methanol and water as eluent. There was thus obtained the required starting material (0.2 g; recrystallised from a mixture of hexane and ethyl acetate).

NMR Spectrum (CDCl$_3$, δ values) 1.64 (s, 6H), 1.65 (s, 6H), 7.0 (d, 1H), 7.6 (d, 1H), 7.9 (q, 1H).

EXAMPLE 28

Using a similar procedure to that described in Example 14, 4-methoxy-4-[3-(1,1,3,3-tetramethyl-2,2-dioxo-1,3-dihydrobenzo[c]thien-5-ylthio)phenyl]tetrahydropyran was oxidised with potassium peroxymonosulphate to give 4-methoxy-4-[3-(1,1,3,3-tetramethyl-2,2-dioxo-1,3-dihydrobenzo[c]thien-5-ylsulphonyl)phenyl]-tetrahydropyran in 80% yield, m.p. 115° C.

NMR Spectrum (CDCl$_3$, δ values) 1.68 (s, 6H), 1.72 (s, 6H), 2.0 (m, 4H), 2.95 (s, 3H), 3.85 (m, 4H), 7.4–8.0 (m, 7H).

EXAMPLE 29

Using a similar procedure to that described in Example 3, (2RS,4SR)-2-ethyl-4-hydroxy-4-[3-(4-tert-butyl-phenylthio)phenyl]tetrahydropyran was reacted with methyl iodide to give (2RS,4SR)-2-ethyl-4-methoxy-4-[3-(4-tert-butylphenylthio)phenyl]tetrahydropyran in 43% yield as an oil.

NMR Spectrum (CDCl$_3$, δ values) 0.95 (t, 3H), 1.3 (s, 9H), 1.5–1.9 (m, 6H), 2.9 (s, 3H), 3.65 (m, 1H), 3.9 (m, 2H), 7.15–7.5 (m, 8H).

The (2RS,4SR)-2-ethyl-4-hydroxy-4-[3-(4-tert-butyl-phenylthio)phenyl]tetrahydropyran used as a starting material was obtained in 17% yield by the reaction of the Grignard reagent from 3-bromophenyl 4-tert-butyl-phenyl sulphide with 2-ethyltetrahydropyran-4-one (*Chem. Ber.*, 1955, 88, 1053) using the procedure described in Note e. below Table IV in Example 9. There were thus obtained the required (2RS,4SR)-diastereoisomer, NMR Spectrum (CDCl$_3$, δ values) 0.95 (t, 3H), 1.3 (s, 9H), 1.5–1.78 (m, 6H), 3.7 (m, 1H), 3.9 (m, 2H), 7.15–7.5 (m, 8H); and the corresponding (2SR,4SR)-diastereoisomer in 35% yield, NMR Spectrum (CDCl$_3$, δ values) 0.9 (t, 3H), 1.4 (s, 9H), 1.5–1.9 (m, 4H), 2.3 (m, 2H), 3.3 (m, 2H), 3.9 (m, 1H), 7.15–7.4 (m, 8H).

EXAMPLE 30

Using a similar procedure to that described in Example 3, (2SR,4SR)-2-ethyl-4-hydroxy-4-[3-(4-tert-butyl-phenylthio)phenyl]tetrahydropyran was reacted with methyl iodide to give (2SR,4SR)-2-ethyl-4-methoxy-4-[3-(4-tert-butylphenylthio)phenyl]tetrahydropyran in 57% yield as an oil.

NMR Spectrum (CDCl$_3$, δ values) 0.8 (t, 3H), 1.3 (s, 9H), 1.5–1.9 (m, 4H), 2.3 (m, 2H), 2.85 (s, 3H), 3.3 (m, 2H), 3.9 (m, 1H), 7.15–7.4 (m, 8H).

EXAMPLE 31

A solution of (2S,4R)-4-[3-(4-tert-butylphenylthio)-phenyl]-4-hydroxy-2-methyltetrahydropyran (0.85 g) in DMF (10 ml) was added to sodium hydride (50% w/w dispersion in mineral oil; 0.36 g) and the mixture was stirred at ambient temperature for 30 minutes. Methyl iodide (0.5 ml) was added and the mixture was stirred at ambient temperature for 18 hours. The mixture was poured into water and acidified by the addition of 2N hydrochloric acid solution. The mixture was extracted with diethyl ether (2×30 ml). The combined extracts were washed with water, dried (MgSO$_4$) and evaporated. The residue was purified by column chromatography using a 5:1 v/v mixture of hexane and ethyl acetate as eluent. There was thus obtained (2S,4R)-4-[3-(4-tert-butylphenylthio)phenyl]-4-methoxy-2-methyltetrahydropyran (0.76 g, 86%) as an oil, $[\alpha]^{20} = +1.2$ (chloroform, c=1 g/100 ml).

The (2S,4R)-4-[3-(4-tert-butylphenylthio)phenyl]-4-hydroxy-2-methyltetrahydropyran used as a starting material was obtained as follows:

A Grignard reagent was prepared by heating a mixture of 3-bromophenyl 4-tert-butylphenyl sulphide (1.9 g), magnesium turnings (0.16 g), iodine (5 mg) and diethyl ether (9 ml) to reflux for 2 hours. The mixture was cooled to ambient temperature and a solution of (2S)-2-methyltetrahydropyran-4-one (0.65 g) in diethyl ether (2 ml) was added. The mixture was stirred at ambient temperature for 40 minutes. The mixture was poured into water (100 ml), neutralised by the addition of 2N aqueous hydrochloric acid solution, and extracted with diethyl ether (2×25 ml). The combined extracts were washed with water, dried (MgSO₄) and evaporated. The residue was purified by column chromatography using a 3:1 v/v mixture of hexane and ethyl acetate as eluent. There was thus obtained the required starting material (0.88 g, 42%), as an oil.

NMR Spectrum (CDCl₃, δ values) 1.2 (d, 3H), 1.3 (s, 9H), 1.6–1.8 (m, 3H), 2.0–2.15 (m, 1H), 3.8–4.1 (m, 3H), 7.1–7.5 (m, 8H).

The (2S)-2-methyltetrahydropyran-4-one, used as a starting material above, was obtained as follows:

Sodium bis-(2-methoxyethoxy)aluminium hydride (3.4M in toluene, 200 ml) was added over a period of 30 minutes to a solution of (−)-(2S,3S,4S)-2,3-epoxyhept-6-en-4-ol (29 g; *J. Org. Chem.*, 1983, 48, 5093, compound No. (−)14 therein) in tetrahydrofuran (1100 ml) which had been cooled to −15° C. and the mixture was stirred for 16 hours and allowed to warm to ambient temperature. The mixture was cooled in an ice-bath and dilute aqueous sulphuric acid (10% w/v, 1350 ml) was added slowly. Sodium chloride was added to produce two phases. The organic phase was separated and the aqueous phase was extracted with ethyl acetate. The combined organic phases were washed with a saturated aqueous sodium chloride solution, dried (MgSO₄) and evaporated. The residue was purified by column chromatography using a 2:3 v/v mixture of hexane and ethyl acetate as eluent. There was thus obtained (2S,4S)-hept-6-ene-2,4-diol (20 g, 67%), as an oil.

NMR Spectrum (CDCl₃, δ values) 1.23 (d, 3H), 1.63 (t, 2H), 2.18–2.4 (m, 4h), 3.93–4.38 (m, 2H), 5.08–5.25 (m, 2H), 5.70–5.96 (m, 1H).

A solution of a portion (5.6 g) of the product so obtained in methanol (875 ml) was cooled to −20° C. and a stream of ozone-containing oxygen (approximately 5% ozone) was bubbled into the solution for 130 minutes. Oxygen gas and then argon were bubbled into the solution to remove any excess ozone. Dimethyl sulphide (20 ml) was added and the mixture was allowed to warm to ambient temperature. The mixture was evaporated and the residue was purified by column chromatography using ethyl acetate as eluent. There was thus obtained as a mixture of diastereoisomers (2S,4R,6R)- and (2S,4R,6S)-4,6-dihydroxy-2-methyltetrahydropyran (3.7 g, 67%), as an oil.

After repetition of the above steps, a saturated solution of hydrogen chloride in ethanol (90 drops) was added to a solution of the product so obtained (19 g) in ethanol (90 ml) which had been cooled in an ice-bath and the mixture was stored at 5° C. for 16 hours. The mixture was evaporated to give as a mixture of diastereoisomers (2S,4R,6R)- and (2S,4R,6S)-6-ethoxy-4-hydroxy-2-methyltetrahydropyran in quantitative yield, as an oil, which was used without further purification.

A solution of the product so obtained in dimethylformamide (45 ml) was cooled to 0° C. and there were added in turn imidazole (20.4 g) and molecular sieve (4 Angstrom, 5 g). Triethylsilyl chloride (24.3 ml) was added dropwise and the mixture was stirred at 0° C. for 2 hours. The mixture was poured onto ice and an ethyl acetate extract was taken. The organic phase was dried (MgSO₄) and evaporated. The residue was dissolved in ether (300 ml) and the solution was washed with cold water. The organic layer was separated, dried (MgSO₄) and evaporated to give as a mixture of diastereoisomers (2S,4R,6R)- and (2S,4R,6S)-6-ethoxy-2-methyl-4-triethylsilyloxytetrahydropyran (36 g, 91%), which was used without further purification.

Triethylsilane (15.7 g) and trimethylsilyl trifluoromethanesulphonate (29.1 g) were added in turn to a solution of the product so obtained in methylene chloride (300 ml) which had been cooled to 5° C. and the mixture was stirred at 5° C. for 30 minutes. The mixture was poured into ice-cold water (50 ml) and the resultant mixture was stirred for 5 minutes. The mixture was neutralised by the portionwise addition of sodium bicarbonate. The organic layer was separated and the aqueous layer was saturated with sodium chloride and extracted with ethyl acetate. The organic solutions were combined, dried (MgSO₄) and evaporated. The residue was purified by column chromatography using a 4:1 v/v mixture of hexane and ethyl acetate as eluent. There was thus obtained (2S,4S)-4-hydroxy-2-methyltetrahydropyran (6.2 g, 41%).

NMR Spectrum (CDCl₃, δ values) 1.15–1.25 (m, 4H), 1.4–1.6 (m, 1H), 1.8–2.0 (m, 2H), 3.3–3.5 (m, 2H), 3.7–3.8 (m, 1H), 4.0 (m, 1H).

Jones reagent (*J. Chem. Soc*, 1951, 2407; 13.3 ml of a 8M solution of chromium trioxide in aqueous sulphuric acid) was added dropwise to a solution of the product so obtained in acetone (250 ml) which was cooled to 5° C. Isopropanol (approximately 20 drops) was added to destroy the excess of oxidant and the mixture was stirred at ambient temperature for 30 minutes. The mixture was filtered and the filtrate was evaporated. The residue was dissolved in diethyl ether (10 ml) and the solution was filtered through Kieselgel 60H silica and evaporated. There was thus obtained (2S)-2-methyltetrahydropyran-4-one (4.85 g, 81%), as an oil.

NMR Spectrum (CDCl₃, δ values) 1.3 (d, 3H), 2.2–2.7 (m, 4H), 3.6–3.8 (m, 2H), 4.2–4.3 (m, 1H).

EXAMPLE 32

A solution of (2S,4R)-4-[5-fluoro-3-(4-tert-butylphenylthio)phenyl]-4-hydroxy-2-methyltetrahydropyran (0.54 g) in DMF (7 ml) was added to sodium hydride (50% w/w dispersion in mineral oil; 0.25 g) and the mixture was stirred at ambient temperature for 30 minutes. Methyl iodide (0.35 ml) was added and the mixture was stirred at ambient temperature for 2 hours. The mixture was poured into water and brought to pH7 by the addition of 2N aqueous hydrochloric acid solution. The mixture was extracted with diethyl ether (2×20 ml). The combined extracts were washed with water, dried (MgSO₄) and evaporated. The residue was purified by column chromatography using a 5:1 v/v mixture of hexane and ethyl acetate as eluent. There was thus obtained (2S,4R)-4-[3-(5-fluoro-4-tert-butylphenylthio)phenyl]-4-methoxy-2-methyltetrahydropyran (0.47 g, 84%), m.p. 50°–51° C. (recrystallised from a mixture of methanol and water), [α]$^{20}$ = +1.8 (chloroform, c=1 g/100 ml).

The (2S,4R)-4-[5-fluoro-3-(4-tert-butylphenylthio)phenyl]-4-hydroxy-2-methyltetrahydropyran used as a starting material was obtained as follows:

A solution of 3-bromo-5-fluorophenyl 4-tert-butylphenyl sulphide (2.03 g) in THF (18 ml) was cooled to −60° C. and n-butyl-lithium (1.6M in hexane, 3.8 ml) was added. The mixture was stirred at −60° C. for 5 minutes. A 0.5M solution of magnesium bromide in a 1:1 v/v mixture of toluene and diethyl ether (15 ml) [obtained by the reaction of magnesium turnings (2.6 g) and ethylene bromide (8.6 ml) in a mixture of diethyl ether (50 ml) and toluene (25 ml) followed by the addition of diethyl ether (75 ml) and toluene (50 ml)] was added and the mixture was allowed to warm to 4° C. A solution of (2S)-2-methyltetrahyrdopyran-4-one (0.57 g) in THF (10 ml) was added and the mixture was stirred at 4° C. for 15 minutes. The mixture was poured into water (30 ml) and extracted with diethyl ether (2×25 ml). The combined extracts were washed with water, dried (MgSO$_4$) and evaporated. The residue was purified by column chromatography using increasingly polar mixtures of hexane and ethyl acetate as eluent. There was thus obtained the required starting material (0.59 g, 30%), as an oil.

NMR Spectrum (CDCl$_3$, δ values) 1.2 (d, 3H), 1.35 (s, 9H), 1.5–1.7 (m, 3H), 1.9–2.1 (m, 1H), 3.8–4.0 (m, 3H), 6.7–7.4 (m, 7H).

EXAMPLE 33

A mixture of (2RS,3SR)-3-[5-fluoro-3-(4-tert-butylphenylthio) phenyl]-3-hydroxy-2-methyltetrahydrofuran (0.25 g), sodium hydride (60% w/w dispersion in mineral oil, 0.042 g), 15-crown-5 (0.005 g) and THF (5 ml) was stirred at ambient temperature for 5 minutes. Methyl iodide (0.3 g) was added and the mixture was stirred at ambient temperature for 15 hours. The mixture was partitioned between diethyl ether and water. The organic phase was washed with brine, dried (MgSO$_4$) and evaporated. The residue was purified by column chromatography using methylene chloride as eluent. There was thus obtained (2RS,3SR)-3-[5-fluoro-3-(4-tert-butylphenylthio)phenyl]-3-methoxy-2-methyltetrahydrofuran (0.176 g, 68%), as an oil.

NMR Spectrum (CDCl$_3$, δ values) 1.13 (d, 3H), 1.33 (s, 9H), 2.25–2.5 (m, 2H), 3.13 (s, 3H), 3.5–4.25 (m, 3H), 6.6–7.0 (m, 3H), 7.38 (s, 4H).

The (2RS,3SR)-3-[5-fluoro-3-(4-tert-butylphenylthio)phenyl]-3-hydroxy-2-methyltetrahydrofuran used as a starting material was obtained as follows:

A Grignard reagent was prepared by stirring a mixture of 3-bromo-5-fluorophenyl 4-tert-butylphenyl sulphide (0.05 g), magnesium powder (0.039 g), a crystal of iodine and THF (1 ml) at ambient temperature for 1 hour. A solution of 2-methyltetrahydrofuran-3-one (0.162 g) in THF (0.15 ml) was added and the mixture was stirred at ambient temperature for 15 hours. The mixture was partitioned between diethyl ether and water. The organic phase was washed with brine, dried (MgSO$_4$) and evaporated. The residue was purified by column chromatography using methylene chloride as eluent. There was thus obtained the required starting material (0.17 g, 32%) as an oil, having the 2-methyl and 3-hydroxy groups in a cis-relationship.

EXAMPLE 34

Using a similar procedure to that described in Example 33, (2RS,4SR)-3-[5-fluoro-3-(naphth-2-ylthio)phenyl]-3-hydroxy-2-methyltetrahydrofuran was reacted with methyl iodide to give (2RS,3SR)-3-[5-fluoro-3-(naphth-2-ylthio)phenyl]-3-methoxy-2-methyltetrahydrofuran in 58% yield as an oil.

NMR Spectrum (CDCl$_3$, δ values) 1.15 (d, 3H), 2.25–2.6 (m, 2H), 3.15 (s, 3H), 3.5–4.5 (m, 3H), 6.75–8.0 (m, 10H).

The (2RS,3SR)-3-[5-fluoro-3-(naphth-2-ylthio)phenyl]-3-hydroxy-2-methyltetrahydrofuran used as a starting material was obtained as follows:

The procedure described in the last two paragraphs in Note b. below Table III in Example 8 were repeated except that 2-methyltetrahydrofuran-3-one was used in place of tetrahydropyran-4-one. There was thus obtained the required starting material in 30% yield as an oil.

EXAMPLE 35

Using a similar procedure to that described in Example 14, 4-[3-(3-chloro-4-(N-methyl)acetamidophenylthio)phenyl]-4-methoxytetrahydropyran was oxidised with potassium peroxymonosulphate to give 4-[3-(3-chloro-4-(N-methyl)acetamidophenylsulphonyl)phenyl]-4-methoxytetrahydropyran in 87% yield, m.p. 119°–121° C. (triturated under a mixture of hexane and diethyl ether).

EXAMPLE 36

Sodium hydride (60% w/w dispersion in mineral oil; 0.12 g) was added to a mixture of 4-[3-(3-chloro-4-trifluoroacetamidophenylthio)phenyl]-4-methoxytetrahydropyran (0.77 g) and DMF (4 ml) and the mixture was stirred at ambient temperature for 45 minutes. Methyl iodide (0.36 ml) was added and the mixture was stirred at ambient temperature for 1 hour. A second portion of sodium hydride (60%, 0.11 g) was added and, after 1 hour, a second portion of methyl iodide (0.36 ml) was added and the mixture was stirred at ambient temperature for 16 hours.

A 2N sodium hydroxide solution (4 ml) was added and the mixture was stirred at ambient temperature for 45 minutes. The mixture was partitioned between diethyl ether and water. The organic phase was washed with water, dried (MgSO$_4$) and evaporated. The residue was purified by column chromatography using increasingly polar mixtures of hexane and ethyl acetate as eluent. There was thus obtained 4-[3-(chloro-4-dimethylaminophenylthio)phenyl]-4-methoxytetrahydropyran (0.19 g, 31%) as a gum.

NMR Spectrum (CDCl$_3$, δ values) 1.05–2.05 (m, 4H), 2.85 (s, 6H), 2.95 (s, 3H), 3.75–3.9 (m, 4H), 7.0 (d, 1H), 7.12–7.42 (m, 6H).

The 4-[3-(3-chloro-4-trifluoroacetamidophenylthio)phenyl]-4-methoxytetrahydropyran used as a starting material was obtained in 23% yield, as an oil by the coupling of 2'-chloro-4'-iodo-2,2,2-trifluoroacetanilide and 4-(3-mercaptophenyl)-4-methoxytetrahydropyran using a similar procedure to that described in Example 12.

NMR Spectrum (CDCl$_3$, δ values) 1.88–2.08 (m, 4H), 2.96 (s, 3H), 3.78–3.9 (m, 4H), 7.2–7.45 (m, 6H), 8.25 (d, 1H).

EXAMPLE 37

Using a similar procedure to that described in Example 3, 4-[4-(4-tert-butylphenylthio)phenyl]-4-hydroxytetrahydropyram was reacted with methyl iodide give 4-[4-(4-tert-butylphenylthio)phenyl]-4-methoxytetrahydropyran in 78% yield as an oil.

NMR Spectrum (CDCl$_3$, δ values) 1.30 (s, 9H), 1.85–2.08 (m, 4H), 2.95 (s, 3H), 3.75–3.92 (m, 4H), 7.22–7.38 (m, 8H).

The 4-[4-(4-tert-butylphenylthio)phenyl]-4-hydroxytetrahydropyran used as a starting material was obtained as follows:

Using a similar procedure to that described in Example 1, 4-tert-butylphenylthiol was reacted with 1,4-dibromobenzene to give 4-bromophenyl 4-tert-butylphenyl sulphide in 59% yield, m.p. 39°–46° C.

Using a similar procedure to that described in the first paragraph of the portion of Example 1 which is concerned with the preparation of starting materials the product so obtained was reacted with tetrahydropyran-4-one to give the required starting material in 66% yield, m.p. 103°–105° C.

EXAMPLE 38

Using a similar procedure to that described in Example 18, 4-[3-(4-acetamido-3-chlorophenylthio)phenyl]-4-methoxytetrahydropyran was reacted with methyl bromoacetate to give 4-[3-(3-chloro-4-(N-methoxycarbonylmethyl)acetamidophenylthio)phenyl]-4-methoxytetrahydropyran in 37% yield as a gum.

NMR Spectrum (CDCl$_3$, δ values) 1.88 (s, 3H), 1.90–2.10 (m, 4H), 3.0 (s, 3H), 3.58 (d, 1H), 3.72 (s, 3H), 3.75–3.80 (m, 4H), 5.02 (d, 1H), 7.10 (doublet of doublets, 1H), 7.25 (m, 2H), 7.27 (m, 1H), 7.42 (m, 3H).

EXAMPLE 39

Using a similar procedure to that described in Example 18, 4-[3-(3-chloro-4-propionamidophenylthio)phenyl]-4-methoxytetrahydropyran was reacted with methyl iodide to give 4-[3-(3-chloro-4-(N-methylpropionamido)phenylthio)phenyl]-4-methoxytetrahydropyran in 67% yield as a gum.

NMR Spectrum (CDCl$_3$ δ values) 1.05 (t, 3H), 1.9–2.1 (m, 6H), 2.95 (s, 3H), 3.15 (s, 3H), 3.8–3.9 (m, 4H), 7.14 (m, 2H), 7.27 (m, 1H), 7.42 (m, 3H), 7.55 (broad s, 1H).

The 4-[3-(3-chloro-4-propionamidophenylthio)phenyl]-4-methoxytetrahydropyran used as a starting material was obtained as follows:

The procedure described in the last paragraph of Example 23 was repeated except that propionyl chloride was used in place of acetyl chloride. There was thus obtained 2-chloro-4-iodopropionanilide in 76% yield; m.p. 139°–140° C.

The procedure described in Example 12 was repeated except that 2-chloro-4-iodopropionanilide was used in place of 4-bromoiodobenzene. There was thus obtained the required starting material in 32% yield as a gum.

NMR Spectrum (CDCl$_3$, δ values) 1.28 (t, 3H), 1.88–2.05 (m, 4H), 2.48 (q, 2H), 2.95 (s, 3H), 3.78–3.90 (m, 4H), 7.27–7.48 (m, 6H), 8.40 (d, 1H).

EXAMPLE 40

The acetylation procedure described in the last paragraph of Example 23 was repeated except that 4-[3-(3-chloro-4-N-(2,2,2-trifluoroethyl)aminophenylthio)-phenyl]-4-methoxytetrahydropyran was used in place of 2-chloro-4-iodoaniline. There was thus obtained 4-[3-(3-chloro-4-(N-(2,2,2-trifluoroethyl)acetamido)phenylthio)phenyl]-4-methoxytetrahydropyran in 69% yield as a gum.

NMR Spectrum (CDCl$_3$, δ values) 1.85 (s, 3H), 1.9–2.1 (m, 4H), 2.98 (s, 3H), 3.58 (m, 1H), 3.9–3.94 (m, 4H), 4.95 (m, 1H), 7.1 (doublet of doublets, 1H), 7.27 (m, 2H), 7.43 (m, 3H), 7.55 (m, 1H).

The 4-[3-(3-chloro-4-N-(2,2,2-trifluoroethyl)aminophenylthio)phenyl]-4-methoxytetrahydropyran used as a starting material was obtained as follows:

A mixture of 2-chloro-4-iodotrifluoroacetanilide (1.65 g), borane-THF complex (1M, 9.45 ml) and THF (4 ml) was heated to reflux for 2.5 hours. The mixture was cooled to ambient temperature. A second portion of borane-THF complex (1M, 4.7 ml) was added and the mixture was heated to reflux for 2.5 hours. The mixture was cooled to ambient temperature and poured onto a mixture of ice and water (30 ml). The mixture was acidified to pH1 by the addition of concentrated hydrochloric acid and stirred at ambient temperature for 30 minutes. The mixture was then basified to pH14 by the addition of sodium hydroxide pellets. The mixture was stirred for 90 minutes and extracted with methylene chloride. The organic phase was washed with water, dried (MgSO$_4$) and evaporated. The residue was purified by column chromatography using increasingly polar mixtures of hexane and ethyl acetate as eluent. There was thus obtained 2-chloro-4-iodo-N-(2,2,2-trifluoroethyl)aniline (0.46 g) as a solid.

NMR Spectrum (CDCl$_3$, δ values) 3.8 (m, 2H), 6.52 (d, 1H), 7.45 (m, 1H), 7.58 (d, 1H).

The procedure described in Example 12 was repeated except that 2-chloro-4-iodo-N-(2,2,2-trifluoroethyl)aniline was used in place of 4-bromoiodobenzene. There was thus obtained the required starting material in 61% yield as a gum.

NMR Spectrum (CDCl$_3$, δ values) 1.85–2.08 (m, 4H), 2.95 (s, 3H), 3.75–3.95 (m, 6H), 6.75 (d, 1H), 7.05 (d, 1H), 7.15–7.35 (m, 4H), 7.45 (m, 1H).

EXAMPLE 41

Using a similar procedure to that described in Example 18, 4-[3-(4-acetamido-2-chlorophenylthio)phenyl]-4-methoxytetrahydropyran was reacted with methyl iodide to give 4-[3-(2-chloro-4-N-methylacetamidophenylthio)phenyl]-4-methoxytetrahydropyran in 68% yield as a gum.

NMR Spectrum (CDCl$_3$, δ values) 1.85–2.1 (m, 7H), 2.98 (s, 3H), 3.25 (s, 3H), 3.8–3.9 (m, 4H), 6.85–6.95 (m, 2H), 7.27 (m, 1H), 7.4–7.5 (m, 3H), 7.55 (s, 1H).

The 4-[3-(4-acetamido-2-chlorophenylthio)phenyl]-4-methoxytetrahydropyran used as a starting material was obtained as follows:

The acetylation procedure described in the last paragraph of Example 23 was repeated except that 3-chloro-4-iodoaniline was used in place of 2-chloro-4-iodoaniline. There was thus obtained 3-chloro-4-iodoacetanilide in 43% yield, m.p. 125°–127° C.

The procedure described in Example 12 was repeated except that 3-chloro-4-iodoacetanilide was used in place of 4-bromoiodobenzene. There was thus obtained the required starting material in 60% yield as a gum.

NMR Spectrum (CDCl$_3$, δ values) 1.85–2.1 (m, 4H), 2.18 (s, 3H), 2.95 (s, 3H), 3.75–3.9 (m, 4H), 7.12 (d, 1H), 7.18–7.42 (m, 5H), 7.7 (m, 1H).

EXAMPLE 42

Using a similar procedure to that described in the last paragraph of Example 23, 4-[3-(4-amino-3-chlorophenylthio)phenyl]-4-methoxytetrahydropyran was reacted with benzoyl chloride to give, after purification of the reaction mixture by column chromatography using increasingly polar mixtures of hexane and ethyl acetate as eluent, 4-[3-(4-benzamido-3-chlorophenylthio)phenyl]-4-methoxytetrahydropyran in 86% yield as a gum.

NMR Spectrum (CDCl$_3$, δ values) 1.85–2.1 (m, 4H), 2.95 (s, 3H), 3.78–3.9 (m, 4H), 7.2–7.65 (m, 9H), 7.92 (m, 2H), 8.55 (d, 1H).

EXAMPLE 43

Using a similar procedure to that described in Example 18, 4-[3-(4-benzamido-3-chlorophenylthio)phenyl]-4-methoxytetrahydropyran was reacted with methyl iodide to give 4-[3-(3-chloro-4-(N-methylbenzamido)phenylthio)phenyl]-4-methoxytetrahydropyran in 86% yield as a gum.

NMR Spectrum (CDCl$_3$, δ values) 1.86–2.05 (m, 4H), 2.95 (s, 3H), 3.45 (s, 3H), 3.78–3.90 (m, 4H), 6.95 (m, 2H), 7.15–7.45 (m, 10H).

EXAMPLE 44

The following illustrate representative pharmaceutical dosage forms containing the compound of formula I, or a pharmaceutically-acceptable salt salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |
| (b) Tablet II | |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |
| (d) Capsule | mg/capsule |
| Compound X | 10 mg |
| Lactose Ph.Eur | 488.5 |
| Magnesium stearate | 1.5 |
| (e) Injection I | (50 mg/ml) |
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |
| (f) Injection II | (10 mg/ml) |
| Compound X | 1.0% w/v |
| Sodium phosphate BP | 3.6% w/v |
| 0.1M Sodium hydroxide solution | 15.0% v/v |
| Water for injection to 100% | |
| (g) Injection III | (1 mg/ml, buffered to pH 6) |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |
| (h) Aerosol I | mg/ml |
| Compound X | 10.0 |
| Sorbitan trioleate | 13.5 |
| Trichlorofluoromethane | 910.0 |
| Dichlorodifluoromethane | 490.0 |
| (i) Aerosol II | |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |
| (j) Aerosol III | |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| (k) Aerosol IV | |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

Note
The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE

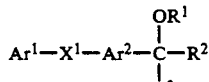

I

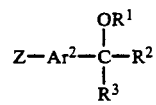

II

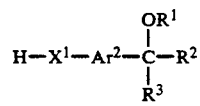

III

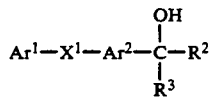

IV

SCHEME I

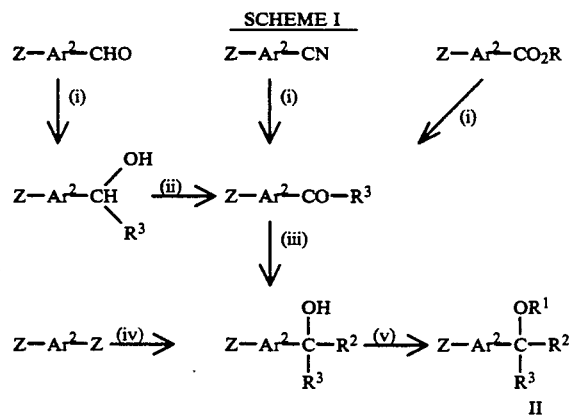

II

SCHEME I

Reagents
(i) R³Li or R³MgZ, THF
(ii) DDQ or MnO₂
(iii) R²Li or R²MgZ, THF;
(iv) BuLi or Mg, THF; R²COR³, THF
(v) R¹Z, base Note
R = (1-4C)alkyl such as Me or Et

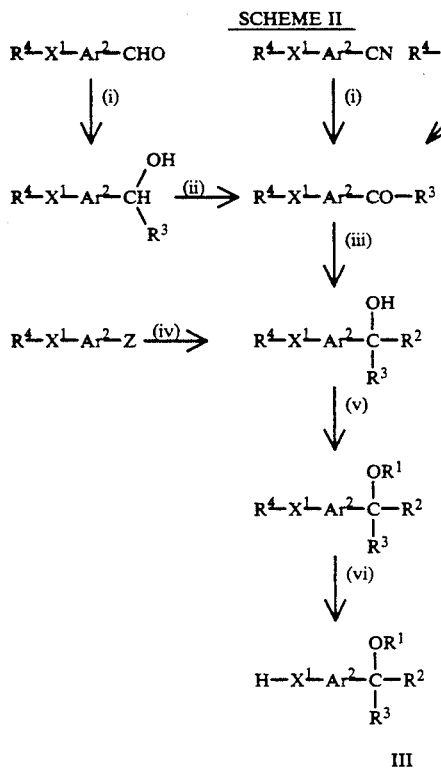

SCHEME II

III

Reagents
(i) to (v) as in Scheme I
(vi) Conventional removal of the protecting group R⁴ which is, e.g. COMe, THP, CH₂Ph or Me.

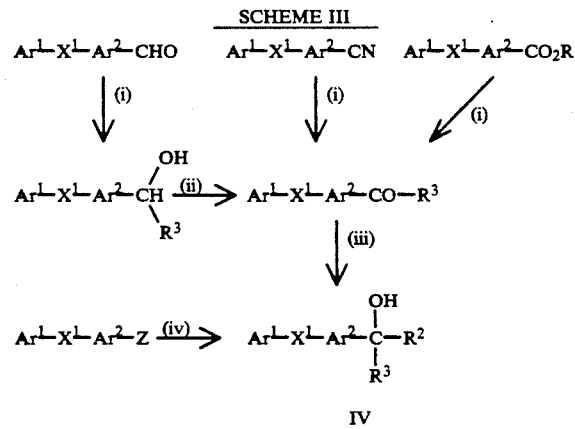

SCHEME III

IV

Reagents
(i) to (iv) as in Scheme I

What we claim is:

1. A diaryl ether heterocycle of the formula I

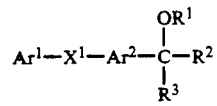

wherein Ar¹ is phenyl or naphthyl which may optionally bear one or more substituents selected from amino, halogeno, hydroxy, cyano, (1-6C)alkyl, (2-6C)alkenyl, (2-6C)alkynyl, (1-4C)alkoxy, (1-4C)alkylthio, (1-4C)alkysulphinyl, (1-4C)alkylsulphonyl, (1-4C)alkylamino, di-[(1-4C)alkyl]amino, (1-4C)alkoxycarbonyl, (2-4C)alkanoyl, hydroxy-(1-6C)alkyl, fluoro-(1-4C)alkyl, cyano-(1-6C)alkyl, fluoro-(1-4C)alkoxy, cyano-(1-4C)alkoxy, (1-4C)alkoxy-(1-4C)alkyl, (1-4C)alkylthio-(1-4C)alkyl, (1-4C)alkylsulphinyl-(1-4C)alkyl, (1-4C)alkylsulphonyl-(1-4C)alkyl, cyano-(4-6C)cycloalkyl, (2-4C)alkanoylamino, N-[(1-4C)alkyl]-(2-4C)alkanoylamino, N-(2,2,2-trifluoroethyl)-(2-4C)alkanoylamino, N-[(1-4C)alkoxycarbonyl-(1-2C)alkyl]-(2-4C)alkanoylamino, trifluoroacetyl, trifluoroacetamido, N-[(1-4C)alkyl]trifluoroacetamido, 2-oxopyrrolidinyl, 1,1,3,3-tetramethyl-2,2-dioxo-2-thiatrimethylene, tri-(1-4C)alkylsilyl, phenyl, benzoyl, benzamido and N-[(1-4C)alkyl]benzamido, and wherein said phenyl, benzoyl, benzamido or N-[(1-4C)alkyl]benzamido substituent may optionally bear a substituent selected from halogeno, (1-4C)alkyl and (1-4C)alkoxy;

wherein X¹ is oxy, thio, sulphinyl or sulphonyl;

wherein Ar² is phenylene which may optionally bear one or two substituents selected from halogeno, hydroxy, amino, nitro, cyano, carbamoyl, (1-4C)alkyl, (3-4C)alkenyloxy, (1-4C)alkoxy, (1-4C)alkylthio, (1-4C)alkylsulphinyl, (1-4C)alkylsulphonyl, (1-4C)alkylamino, di-[(1-4C)alkyl]amino, fluoro-(1-4C)alkyl, cyano-(1-4C)alkyl, (1-4C)alkoxycarbonyl, N-[(1-4C)alkyl]carbamoyl, N,N-di-[(1-4C)alkyl]carbamoyl, (2-4C)alkanoylamino, fluoro-(1-4C)alkoxy, cyano-(1-4C)alkoxy, carbamoyl-(1-4C)alkoxy, amino-(2-4C)alkoxy, (1-4C)alkylamino-(2-4C)alkoxy, di-[(1-4C)alkyl]amino-(2-4C)alkoxy and (1-4C)alkoxycarbonyl-(1-4C)alkoxy;

wherein R¹ is (1-6C)alkyl, (3-6C)alkenyl, (3-6C)alkynyl, cyano-(1-4C)alkyl or (2-4C)alkanoyl, or R¹ is benzoyl which may optionally bear a substituent selected from halogeno, (1-4C)alkyl and (1-4C)alkoxy; and wherein R² and R³ together form a group of the formula —A²—X²—A³— which, together with the carbon atom to which A² and A³ are attached, defines a ring having 4 to 7 ring atoms, wherein A² and A³, which may be the same or different, each is (1-4C)alkylene and X² is oxy, and which ring may bear one, two or three substituents, which may be the same or different, selected from halogeno, hydroxy, cyano, (1-4C)alkyl, (1-4C)alkoxy, (1-4C)alkylthio, (1-4C)alkylsulphinyl, (1-4C)alkylsulphonyl and fluoro-(1-4C)alkyl;

or a pharmaceutically-acceptable salt thereof.

2. A diaryl ether heterocycle of the formula I as claimed in claim 1 wherein $Ar^1$ is phenyl, naphth-1-yl or naphth-2-yl which may optionally bear one or two substituents selected from amino, fluoro, chloro, cyano, methyl, tert-butyl, methoxy, methylthio, methylsulphinyl, methylsulphonyl and 2-cyanoprop-2-yl;

$X^1$ is thio, sulphinyl or sulphonyl;

$Ar^2$ is 1,3-phenylene or 1,4-phenylene which may optionally bear one substituent selected from fluoro, hydroxy, amino, nitro, methoxy, methylamino, cyanomethoxy and trifluoromethyl;

$R^1$ is methyl or ethyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy and which ring may bear a substituent selected from fluoro, methyl, methoxy and trifluoromethyl;

or a pharmaceutically-acceptable salt thereof.

3. A diaryl ether heterocycle of the formula I as claimed in claim 1 wherein $Ar^1$ is phenyl or naphth-2-yl which may optionally bear one or two substituents selected from fluoro, chloro, bromo, methyl, ethyl, isopropyl, tert-butyl, methoxy, ethoxy, isopropoxy, methylthio, methylsulphinyl, methylsulphonyl, acetyl, propionyl, isobutyryl, hydroxymethyl, 1-hydroxyethyl, 2-hydroxyethyl, 1-hydroxypropyl, 2-hydroxyprop-2-yl, 3-hydroxypent-3-yl, difluoromethyl, trifluoromethyl, cyanomethyl, 1-cyanoethyl, 2-cyanoethyl, 2-cyanoprop-2-yl, 3-cyanopent-3-yl, trifluoromethoxy, 2,2,2-trifluoroethoxy, methoxymethyl, 1-methoxyethyl, 2-methoxyethyl, 2-methoxyprop-2-yl, methylthiomethyl, 1-methylthioethyl, 2-methylthioethyl, 2-methylthioprop-2-yl, methylsulphinylmethyl, 1-methylsulphinylethyl, 2-methylsulphinylethyl, 2-methylsulphinylprop-2-yl, methylsulphonylmethyl, 1-methylsulphonylethyl, 2-methylsulphonylethyl, 2-methylsulphonylprop-2-yl, 1-cyanocyclopentyl, 1-cyanocyclohexyl, acetamido, propionamido, N-methylacetamido, N-methylpropionamido, trifluoroacetyl, trifluoroacetamido, N-methyltrifluoroacetamido, 2-oxopyrrolidin-1-yl, 1,1,3,3-tetramethyl-2,2-dioxo-2-thiatrimethylene, trimethylsilyl and phenyl;

$X^1$ is oxy, thio, sulphinyl or sulphonyl;

$Ar^2$ is 1,3-phenylene or 1,4-phenylene which may optionally bear one or two substituents selected from fluoro, chloro, bromo, amino, nitro, cyano, methyl, methoxy, methylamino, dimethylamino and trifluoromethyl;

$R^1$ is methyl, ethyl, allyl or 2-propynyl; and $R^2$ and $R^3$ together form a group of the formula —$A^2$—$X^2$—$A^3$— which, together with the carbon atom to which $A^2$ and $A^3$ are attached, defines a ring having 4 to 6 ring atoms, wherein $A^2$ and $A^3$, which may be the same or different, each is methylene or ethylene and $X^2$ is oxy, and which ring may bear one or two substituents selected from fluoro, hydroxy, methyl, ethyl, propyl, methoxy and trifluoromethyl;

or a pharmaceutically-acceptable salt thereof.

4. A diaryl ether heterocycle of the formula I as claimed in claim 1 wherein $Ar^1$ is phenyl or naphth-2-yl which may optionally bear one or two substituents selected from amino, fluoro, chloro, bromo, methyl, ethyl, isopropyl, tert-butyl, methoxy, ethoxy, isopropoxy, methylthio, methylsulphinyl, methylsulphonyl, methylamino, dimethylamino, acetyl, propionyl, isobutyryl, hydroxymethyl, 1-hydroxyethyl, 2-hydroxyethyl, 1-hydroxypropyl, 2-hydroxyprop-2-yl, 3-hydroxypent-3-yl, difluoromethyl, trifluoromethyl, cyanomethyl, 1-cyanoethyl, 2-cyanoethyl, 2-cyanoprop-2-yl, 3-cyanopent-3-yl, trifluoromethoxy, 2,2,2-trifluoroethoxy, methoxymethyl, 1-methoxyethyl, 2-methoxyethyl, 2-methoxyprop-2-yl, methylthiomethyl, 1-methylthioethyl, 2-methylthioethyl, 2-methylthioprop-2-yl, methylsulphinylmethyl, 1-methylsulphinylethyl, 2-methylsulphinylethyl, 2-methylsulphinylprop-2-yl, methylsulphonylmethyl, 1-methylsulphonylethyl, 2-methylsulphonylethyl, 2-methylsulphonylprop-2-yl, 1-cyanocyclopentyl, 1-cyanocyclohexyl, acetamido, propionamido, N-methylacetamido, N-methylpropionamido, N-(2,2,2-trifluoroethyl)acetamido, N-(methoxycarbonylmethyl)acetamido, N-(ethoxycarbonylmethyl)acetamido, trifluoroacetyl, trifluoroacetamido, N-methyltrifluoroacetamido, 2-oxopyrrolidin-1-yl, 1,1,3,3-tetramethyl-2,2-dioxo-2-thiatrimethylene, trimethylsilyl, phenyl, benzoyl, benzamido and N-methylbenzamido, and wherein said phenyl, benzoyl, benzamido or N-methylbenzamido substituent may optionally bear a substituent selected from fluoro, chloro, methyl and methoxy;

$X^1$ is oxy, thio, sulphinyl or sulphonyl;

$Ar^2$ is 1,3-phenylene or 1,4-phenylene which may optionally bear one or two substituents selected from fluoro, chloro, bromo, amino, nitro, cyano, methyl, methoxy, methylamino, dimethylamino and trifluoromethyl;

$R^1$ is methyl, ethyl, allyl or 2-propynyl; and $R^2$ and $R^3$ together form a group of the formula —$A^2$—$X^2$—$A^3$— which, together with the carbon atom to which $A^2$ and $A^3$ are attached, defines a ring having 4 to 6 ring atoms, wherein $A^2$ and $A^3$, which may be the same or different, each is methylene or ethylene and $X^2$ is oxy, and which ring may bear one or two substituents selected from fluoro, hydroxy, methyl, ethyl, propyl, methoxy and trifluoromethyl;

or a pharmaceutically-acceptable salt thereof.

5. A diaryl ether heterocycle of the formula I as claimed in claim 1 wherein $Ar^1$ is phenyl which may optionally bear one or two substituents selected from chloro, isopropyl, tert-butyl, isopropoxy, dimethylamino, acetyl, isobutyryl, 2-hydroxyprop-2-yl, 2-cyanoprop-2-yl, 3-cyanopent-3-yl, 2,2,2-trifluoroethoxy, 2-methoxyprop-2-yl, 1-cyanocyclopentyl, acetamido, N-methylacetamido, propionamido, N-methylpropionamido, N-(methoxycarbonylmethyl)acetamido, trifluoroacetyl, N-methyltrifluoroacetamido, 2-oxopyrrolidin-1-yl, 1,1,3,3-tetramethyl2,2-dioxo-2-thiatrimethylene, trimethylsilyl, phenyl, benzoyl, 4-chlorobenzoyl and N-methylbenzamido; or $Ar^1$ is naphth-2-yl which may optionally bear a substituent selected from fluoro, methyl and trifluoromethyl;

$X^1$ is oxy, thio, sulphinyl or sulphonyl;

$Ar^2$ is 1,3-phenylene which may optionally bear one or two substituents selected from fluoro, chloro, bromo, amino, nitro, cyano, methoxy and trifluoromethyl;

R¹ is methyl, ethyl or allyl; and

R² and R³ together form a group of the formula —A²—X²—A³— which, together with the carbon atom to which A² and A³ are attached, defines a ring having 5 or 6 ring atoms, wherein A² is ethylene, A³ is methylene or ethylene, and X² is oxy, and which ring may bear one or two substituents selected from methyl, ethyl and methoxy;

or a pharmaceutically-acceptable salt thereof.

6. A diaryl ether heterocycle of the formula I as claimed in claim 1 wherein

Ar¹ is 4-t-butylphenyl, 3-(2-cyanoprop-2-yl)phenyl, 4-(2-cyanoprop-2-yl)phenyl, 3-chloro-4-(2-cyanoprop-2-yl)phenyl, 4-(1-cyanocyclopentyl)phenyl, 1,1,3,3-tetramethyl-1,3-dihydrobenzo[c]thien-5-yl, 4-trimethylsilylphenyl, 3-biphenylyl, 4-biphenylyl, 4-benzoylphenyl or naphth-2-yl;

X¹ is oxy, thio or sulphonyl;

Ar² is 1,3-phenylene, 5-fluoro-1,3-phenylene, 2,5-difluoro-1,3-phenylene, 5-bromo-1,3-phenylene or 5-trifluoromethyl-1,3-phenylene;

R¹ is methyl or allyl; and

R² and R³ together form a group of the formula —A²—X²—A³— which, together with the carbon atom to which A² and A³ are attached, defines a ring having 6 ring atoms, wherein each of A² and A³ is ethylene and X² is oxy and which ring may bear a methyl substituent alpha to X²;

or a pharmaceutically-acceptable salt thereof.

7. A diaryl ether derivative of the formula I, or a pharmaceutically-acceptable salt thereof, selected from the group consisting of:

4-methoxy-4-[3-(naphth-2-ylthio)phenyl]tetrahydropyran,

4-[3-(4-t-butylphenylthio)phenyl]-4-methoxytetrahydropyran, 4-methoxy-4-[3-(naphth-2-ylthio)-5-trifluoromethylphenyl] tetrahydropyran and 4-[3-(4-(2-cyanoprop-2-yl)phenylthio)-5-trifluoromethylphenyl]-4-methoxytetrahydropyran.

8. A diaryl ether derivative of the formula I, or a pharmaceutically-acceptable salt thereof, selected from the group consisting of:

4-allyloxy-4-[2,5-difluoro-3-(naphth-2-ylthio)phenyl]-tetrahydropyran, (2RS,4SR)-4-[3-(4-tert-butylphenylthio)phenyl]-4-methoxy-2-methyltetrahydropyran, (2RS,4SR)-4-allyloxy-4-[5-fluoro-3-(4-tert-butylphenoxy)phenyl]-2-methyltetrahydropyran, 4-[3-(3-chloro-4-(2-cyanoprop-2-yl)phenylthio)phenyl]-4-methoxytetrahydropyran, (2S,4R)-4-[3-(4-tert-butylphenylthio)phenyl]-4-methoxy-2-methyltetrahydropyran and (2S,4R)-4-[5-fluoro-3-(4-tert-butylphenylthio)phenyl]-4-methoxy-2-methyltetrahydropyran.

9. A pharmaceutical composition which comprises a 5-lipoxygenase inhibitory amount of a diaryl ether heterocycle of the formula I, or a pharmaceutically-acceptable salt thereof, as claimed in any one of claims 1 to 8 in association with a pharmaceutically-acceptable diluent or carrier.

10. A method of treating a disease or medical condition mediated alone or in part by one or more leukotrienes which comprises administering to a warm-blooded animal requiring such treatment an effective amount of a diaryl ether heterocycle of the formula I, or a pharmaceutically-acceptable salt thereof, as claimed in any one of claims 1 to 8.

* * * * *